US012740794B2

(12) United States Patent
Tafti

(10) Patent No.: US 12,740,794 B2
(45) **Date of Patent: *Sep. 22, 2026**

(54) THROMBECTOMY DEVICE AND METHODS OF USE THEREOF

(71) Applicant: TRANSLATIONAL AND FUNDAMENTAL TECHNOLOGIES INSTITUTE LLC, Encino, CA (US)

(72) Inventor: Bashir Akhavan Tafti, Encino, CA (US)

(73) Assignee: TRANSLATIONAL AND FUNDAMENTAL TECHNOLOGIES INSTITUTE LLC, Encino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/374,167

(22) Filed: Oct. 30, 2025

(65) Prior Publication Data

US 2026/0053515 A1 Feb. 26, 2026

Related U.S. Application Data

(63) Continuation of application No. 18/732,514, filed on Jun. 3, 2024, now Pat. No. 12,484,918.

(60) Provisional application No. 63/505,819, filed on Jun. 2, 2023.

(51) Int. Cl.
*A61B 17/22* (2006.01)
*A61B 17/00* (2006.01)
*A61B 90/00* (2016.01)

(52) U.S. Cl.
CPC ........ *A61B 17/22* (2013.01); *A61B 17/00234* (2013.01); *A61B 90/39* (2016.02); *A61B 2017/00017* (2013.01); *A61B 2017/00238* (2013.01); *A61B 2017/00292* (2013.01); *A61B 2017/00398* (2013.01); *A61B 2017/00867* (2013.01); *A61B 2017/22038* (2013.01); *A61B 2017/22079* (2013.01);
(Continued)

(58) Field of Classification Search
CPC ... A61B 17/22; A61B 17/221; A61B 17/3207; A61B 17/320725; A61B 17/320758; A61B 17/22031; A61B 2017/22034; A61B 2017/22038; A61B 2017/00292
See application file for complete search history.

(56) References Cited

U.S. PATENT DOCUMENTS

| | | | |
|---|---|---|---|
| D301,742 | S | 6/1989 | Wyzgala et al. |
| D337,382 | S | 7/1993 | Wallace |
| 5,295,995 | A | 3/1994 | Kleiman |

(Continued)

FOREIGN PATENT DOCUMENTS

| | | |
|---|---|---|
| CN | 202030669777.3 | 2/2022 |
| CN | 114569185 A | 6/2022 |

(Continued)

OTHER PUBLICATIONS

Argon, Option Elite Filter, Published Aug. 2024, duomed.com. Retrieved from: https://www.duomed.com/sites/default/files/2024-10/ARGON%20OptionElite_Brochure_082024.pdf.

(Continued)

*Primary Examiner* — Diane D Yabut
(74) *Attorney, Agent, or Firm* — Clark & Elbing LLP

(57) ABSTRACT

The present disclosure provides devices and systems for performing thrombectomies and methods of use thereof.

24 Claims, 17 Drawing Sheets

(52) U.S. Cl.
CPC . *A61B 2090/3966* (2016.02); *A61B 2217/005* (2013.01); *A61B 2217/007* (2013.01)

(56) References Cited

U.S. PATENT DOCUMENTS

| | | | |
|---|---|---|---|
| 5,658,308 | A | 8/1997 | Snyder |
| 5,702,413 | A | 12/1997 | Lafontaine |
| 5,766,191 | A | 6/1998 | Trerotola |
| 5,792,154 | A | 8/1998 | Doan et al. |
| 5,935,145 | A | 8/1999 | Villar et al. |
| 6,001,092 | A | 12/1999 | Mirigian et al. |
| 6,033,423 | A | 3/2000 | Ken et al. |
| 6,280,457 | B1 | 8/2001 | Wallace et al. |
| 6,299,627 | B1 | 10/2001 | Eder et al. |
| D452,000 | S | 12/2001 | Crawford et al. |
| D454,637 | S | 3/2002 | Nestenborg |
| D483,869 | S | 12/2003 | Tran et al. |
| 7,220,270 | B2 | 5/2007 | Sawhney et al. |
| 7,938,820 | B2 | 5/2011 | Webster et al. |
| 8,105,309 | B2 | 1/2012 | Kassab et al. |
| 8,123,777 | B2 | 2/2012 | Krolik et al. |
| 8,163,362 | B2 | 4/2012 | Russell |
| D679,804 | S | 4/2013 | White et al. |
| D684,258 | S | 6/2013 | Luethy et al. |
| 8,535,700 | B2 | 9/2013 | Chinn et al. |
| 8,734,374 | B2 | 5/2014 | Aklog et al. |
| 8,784,442 | B2 | 7/2014 | Jones et al. |
| 9,060,802 | B2 | 6/2015 | Kugler et al. |
| 10,117,671 | B2 | 11/2018 | McGuckin, Jr. et al. |
| 10,188,409 | B2 | 1/2019 | Smalling |
| 10,194,928 | B2 | 2/2019 | Yu |
| 10,251,739 | B2 | 4/2019 | Janardhan et al. |
| 10,517,605 | B2 | 12/2019 | Venkatraman et al. |
| 10,641,640 | B2 | 5/2020 | Oh |
| 10,695,159 | B2 | 6/2020 | Hauser |
| 10,786,268 | B2 | 9/2020 | Ben-Ami |
| D903,102 | S | 11/2020 | Seward et al. |
| D913,487 | S | 3/2021 | Orofino |
| 11,013,523 | B2 | 5/2021 | Arad Hadar |
| 11,026,708 | B2 | 6/2021 | Marks et al. |
| 11,027,104 | B2 | 6/2021 | Kume et al. |
| 11,090,078 | B2 | 8/2021 | Walzman |
| 11,185,677 | B2 | 11/2021 | Salahieh et al. |
| 12,484,918 | B2 | 12/2025 | Tafti |
| 12,514,589 | B2 | 1/2026 | Tafti |
| 2001/0046518 | A1 | 11/2001 | Sawhney |
| 2004/0210249 | A1 | 10/2004 | Fogarty et al. |
| 2006/0020285 | A1 | 1/2006 | Niermann |
| 2006/0020286 | A1 | 1/2006 | Niermann |
| 2006/0052823 | A1 | 3/2006 | Mirizzi et al. |
| 2006/0116713 | A1 | 6/2006 | Sepetka et al. |
| 2008/0114391 | A1 | 5/2008 | Dieck et al. |
| 2008/0125798 | A1 | 5/2008 | Osborne et al. |
| 2010/0094320 | A1 | 4/2010 | Arat et al. |
| 2010/0204712 | A1 | 8/2010 | Mallaby |
| 2010/0324590 | A1 | 12/2010 | Johnson et al. |
| 2011/0152920 | A1 | 6/2011 | Eckhouse et al. |
| 2011/0213403 | A1 | 9/2011 | Aboytes |
| 2013/0204278 | A1 | 8/2013 | Cully et al. |
| 2013/0296916 | A1 | 11/2013 | Monstadt et al. |
| 2013/0345739 | A1* | 12/2013 | Brady .................. A61B 17/221 606/200 |
| 2014/0094901 | A1 | 4/2014 | Lorenzo et al. |
| 2014/0121672 | A1 | 5/2014 | Folk |
| 2014/0128905 | A1 | 5/2014 | Molaei |
| 2014/0277006 | A1 | 9/2014 | Bonnette et al. |
| 2014/0309631 | A1 | 10/2014 | McLawhorn et al. |
| 2014/0343595 | A1 | 11/2014 | Monstadt et al. |
| 2015/0359539 | A1 | 12/2015 | Hadley et al. |
| 2016/0143653 | A1* | 5/2016 | Vale ........................ A61F 2/013 606/114 |
| 2016/0166257 | A1 | 6/2016 | Allen et al. |
| 2016/0228128 | A1 | 8/2016 | Connolly |
| 2017/0043066 | A1 | 2/2017 | Laub |
| 2017/0071614 | A1 | 3/2017 | Vale et al. |
| 2018/0271548 | A1 | 9/2018 | Ulm et al. |
| 2019/0000492 | A1 | 1/2019 | Casey et al. |
| 2019/0000500 | A1* | 1/2019 | Masubuchi .... A61B 17/320783 |
| 2019/0142435 | A1 | 5/2019 | DeMeritt |
| 2019/0231355 | A1 | 8/2019 | DeMeritt |
| 2019/0350590 | A1 | 11/2019 | Aboytes et al. |
| 2021/0138194 | A1 | 5/2021 | Garrison et al. |
| 2021/0228224 | A1 | 7/2021 | Razack |
| 2021/0236150 | A1 | 8/2021 | Arad Hadar |
| 2021/0236797 | A1 | 8/2021 | D'Ambrosio et al. |
| 2021/0307767 | A1* | 10/2021 | Gifford, III .......... A61B 17/221 |
| 2022/0192688 | A1 | 6/2022 | Olsen et al. |
| 2024/0081858 | A1 | 3/2024 | Shen |
| 2024/0238580 | A1 | 7/2024 | Swenson |
| 2024/0382208 | A1 | 11/2024 | Tafti |
| 2024/0398429 | A1 | 12/2024 | Tafti |

FOREIGN PATENT DOCUMENTS

| | | |
|---|---|---|
| WO | WO-D235652-001 | 8/2024 |
| WO | WO-D239531-002 | 3/2025 |

OTHER PUBLICATIONS

International Search Report and Written Opinion for International Patent Application No. PCT/US2024/029119, mailed Sep. 17, 2024 (12 pages).

International Search Report and Written Opinion for International Patent Application No. PCT/US2024/032280, mailed Oct. 1, 2024 (13 pages).

Kapur, Mechanical Left Ventricular Unloading to Reduce Infarct Size During Acute Myocardial Infarction, Published: Apr. 2019, Research Gate. Retrieved from: https://www.researchgate.net/publication/332601094_Mehanical_Left_Ventricular_Unloading_to_Reduce_Infarct_Size_During_Acute_Myocardial_Infarction_Insight_from_Preclinical_and_Clinical_Studies.

Malhotra, The MVP Microvascular Plug, Published: Apr. 2016, bmctoday.net. Retrieved from: https://assets/bmctoday.net/evtoday/pdfs/et0416_FT_Medtronic_MVP.pdf.

Sianos, The Recover® LP2.5 catheter-mounted left ventricular assist device, Published: May 20, 2006, eurointervention.pcronline.com, Retrieved from: https://eurointervention.pcronline.com/article/the-recover-lp25-catheter-mounted-left-ventricular-assist-device.

U.S. Appl. No. 29/974,366, Tafti, Bashir Akhavan.

U.S. Appl. No. 29/974,390, Tafti, Bashir Akhavan.

Anonymous, "Okami Medical's LOBO-7 and LOBO-9 Vascular Occluders Receive FDA Clearance," Endovascular Today. (2022) (1 page).

Mangini et al., "Use of Amplatzer Vascular Plug (AVP) in emergency embolisation: preliminary experience and review of literature," Emergency Radiology. 14:153-160 (2008) (2 pages).

Randall et al., "Valve-in-valve transcatheter aortic valve replacement to treat multijet paravalvular regurgitation: A case series and review," Vascular Occluder Devices. (2020) (1 page).

* cited by examiner

THROMBECTOMY DEVICE AND METHODS OF USE THEREOF

BACKGROUND OF THE DISCLOSURE

Arteriovenous fistulas (AVFs) are the gold standard of care for end stage renal disease (ESRD) patients who need to be dialyzed frequently. An AVF is an artificial shunt created by open or minimally invasive surgery wherein an artery and vein are directly connected to each other. Via this connection, the artery provides extra pressure and blood flow into the vein, making it a reliable access for dialysis. Alternatively, a piece of synthetic tubing (i.e., a graft) may be used for creating the shunt between the artery and the vein. Over time, blood clots may form within the venous outflow or the graft and occlude the dialysis access. One method for recanalizing the AVF or arterio-venous graft (AVG) is using rotational thrombectomy devices to break up the clot into smaller pieces and pushing them into the central venous system where they get trapped in the pulmonary capillaries and dissolve. However, the currently available rotational thrombectomy devices have certain limitations. A first class of such devices (e.g., the ARROW-TREROTOLA™ PTDR Device) comprises a self-expanding basket made of shape memory alloys (e.g., Nitinol) which, upon placement within a vessel, expands to conform to the size of the lumen. The basket is then rotated around its longitudinal axis using a motorized handle while being moved forward and backward in the vessel, thereby breaking up the clot into small pieces. This device can be traumatic to the endothelium and induce in-situ thrombosis by exposing the underlying collagen to blood as it has multiple contact points with vessel wall. In addition, it can induce vessel spasm and interfere with the procedure.

A second class of such devices (e.g., the CLEANER™ thrombectomy device) comprises a single sinuous-shaped multifilar wire which is again actuated with a motorized handle to macerate a clot. Although this device is less traumatic to the vessel, it comes with its own shortcomings. First, it breaks the clot into larger pieces which can embolize in larger pulmonary arteries and cause pulmonary embolism. Second, the wire of these devices is pliable and deforms when touching upon subacute or chronic clots which are stiffer in consistency as compared to acute clots. As a result, this device has suboptimal efficacy in breaking up the thrombus.

Finally, a common problem with both classes of rotational thrombectomy devices is that they have very limited efficacy against thrombi entrapped within venous aneurysmal dilations, which are a common phenomenon in dialysis access circuits.

Another application of thrombectomy devices is thrombus retrieval and recanalization of end organ arteries in situations such as acute ischemic stroke (in brain) and acute ischemic myocardial infarction (in the heart). These thrombectomy devices, which are commonly referred to as stent retrievers, are now the standard of care in management of acute ischemic stroke and myocardial infarction. In such clinical settings, a stent retriever is navigated through a microcatheter and positioned through the blood clot that is occluding the artery. Then, the stent retriever is deployed by pulling back the microcatheter. The stent struts penetrate through the clot and the thrombus gets embedded within the device. When the stent is withdrawn into the catheter, the thrombus captured in the stent cells will be removed together with the stent. Although this technique works very well for removal of acute blood clots, which are relatively soft in consistency and penetrable by the stent struts, it has poor outcomes in approximately one third (⅓) of the cases involving chronic blood clots. Such clots are predominantly composed of fibrotic tissue which is very elastic and does not allow penetration of the stent into the clot substance. Instead, it pushes back against the stent and prevents clot engagement.

Thus, there exists a need for improved thrombectomy devices that address these challenges.

SUMMARY OF THE DISCLOSURE

Described herein are devices, systems, methods, and kits useful for the removal of a vascular occlusion (e.g., a thrombus) from a subject (e.g., a thrombectomy). In particular, the present disclosure features helical thrombectomy devices for use in performing a vascular thrombectomy.

In one aspect, the disclosure features a thrombectomy device comprising a proximal end and a distal end defining a first axis with a length therebetween, wherein: a) the thrombectomy device includes a helical lattice along the first axis, wherein the helical lattice includes a proximal end, a distal end, and a width that extends along a second axis that is perpendicular to the first axis; b) the helical lattice includes a network of lattice cells; and c) the helical lattice is configured to convert between a compressed state (e.g., a deformed state) and an uncompressed state (e.g., a nondeformed state) about the second axis; and wherein the thrombectomy device further comprises a shaft.

In some embodiments, the thrombectomy device is sized to traverse a blood vessel. In some embodiments, the helical lattice includes 1 to 25 turns (e.g., from 1 to 10 turns, from 1 to 5 turns, or 3 turns). In some embodiments, each turn includes a pitch from about 1 mm to about 30 mm (e.g., about 1 mm to about 20 mm, about 5 mm to about 20 mm, or about 5 mm to 15 mm). In some embodiments, the helical lattice is compressible about the first axis. In some embodiments, the lattice cells are compressible. In some embodiments, the lattice cells comprise a polygonal, square, rectangular, triangular, diamond, circular, elliptical, oval, oblong, lens, asteroid, deltoid, slit, or amorphous shape. In some embodiments, the helical lattice (e.g., the material forming the structure of the helical lattice) includes a thickness from about 0.01 mm to about 1 mm (e.g., a thickness from about 0.03 mm to about 0.8 mm, a thickness from about 0.05 mm to about 0.6 mm, a thickness from about 0.1 mm to about 0.4 mm, or a thickness from about 0.2 mm to about 0.3 mm).

In some embodiments, the helical lattice is self-expanding from the compressed state to the uncompressed state (e.g., the helical lattice is able to return to its pre-deformed or non-compacted shape once the compression force is removed). In some embodiments, the helical lattice is flexible. In some embodiments, the helical lattice includes two outer edges, wherein the lattice cells are disposed between the two outer edges. In some embodiments, the two outer edges are fixedly attached to the shaft at one or more locations. In some embodiments, the one or more locations include the proximal end of the thrombectomy device or the distal end of the thrombectomy device, or both.

In some embodiments, the width of the thrombectomy device is from about 1 mm to about 30 mm (e.g., from about 1 mm to about 20 mm, from about 5 mm to about 20 mm, from about 5 mm to about 15 mm. etc.). In some embodiments, the width of the thrombectomy device is periodic along the length. In some embodiments, the length of the thrombectomy device is from about 10 mm to about 600 mm (e.g., from about 20 mm to about 500 mm, from about 30 mm to about 400 mm, from about 40 mm to about 300 mm, from about 50 mm to about 200 mm, from about 60 mm to about 100 mm, about 80 mm, etc.).

In some embodiments, the shaft extends through the proximal end of the helical lattice and past the distal end of the thrombectomy device. In some embodiments, the shaft includes a lumen extending along the length of the shaft. In some embodiments, the lumen is sized to fit over a guidewire.

In some embodiments, the shaft has a flexural modulus of at least 50 MPa. In some embodiments, the shaft is composed of a plurality of segments. In some embodiments, adjacent segments are configured to rotate independently of each other (e.g., from 0.01° to 45° relative to each other). In some embodiments, each segment has a length of from about 0.1 mm to about 10 mm.

In some embodiments, the thrombectomy device is sized to traverse a blood vessel. In other embodiments, the shaft of the thrombectomy device has a length of from about 1 cm to about 200 cm (e.g., from about 20 cm to about 175 cm, from about 30 cm to about 150 cm, from about 40 cm to about 125 cm, from about 50 cm to about 100 cm, or about 75 cm). In some embodiments, the width of the shaft is from about 1 mm to about 30 mm (e.g., from about 1 mm to about 20 mm, from about 5 mm to about 20 mm, or from about 5 mm to about 15 mm). In some embodiments, the thrombectomy device further includes a radiopaque marker. In some embodiments, the helical lattice includes a shape memory material. In some embodiments, the shape memory material includes nitinol, steel (e.g., stainless steel), or a shape memory polymer. In some embodiments, the thrombectomy device includes a coating.

In some embodiments, the shaft is enclosed within a sheath. In another embodiment, the proximal end of the shaft is enclosed within a housing (e.g., the housing includes a hand-held portion that can be gripped by the operator of the thrombectomy device). In other embodiments, the housing includes an actuator for translating the sheath forwards and backwards along the shaft. In yet other embodiments, the actuator is configured to translate the sheath substantially to the distal end of the thrombectomy device, whereby the sheath covers the thrombectomy device and converts the helical lattice to a compressed state (e.g., causes the helical lattice to deform to a compacted shape along the second axis). In another embodiment, thrombectomy device comprises a distal tip at the distal end that comprises a hollow tapered cone or rubber cap that covers the distal end or is a blunt end. In some embodiments, the shaft is connected to a housing. In some embodiments, the housing includes a sheath, a deployment mechanism configured to retract the sheath, a rotary configured to rotate the shaft and/or the thrombectomy device, and/or an inlet port.

In a second aspect, the disclosure features a delivery system including the thrombectomy device of the first aspect; and a housing (e.g., a housing at a proximal end of the shaft of the thrombectomy device that includes a hand-held portion that can be gripped by the operator of the thrombectomy device and that can be used to manipulate the thrombectomy device) including one or more of inlet ports, a guidewire, a pusher, a sheath, a deployment mechanism configured to retract the sheath into the body of the housing, and a rotator configured to rotate the thrombectomy device. In some embodiments, the shaft of the thrombectomy device is or includes a pusher. In some embodiments, the shaft and/or thrombectomy device is surrounded by the sheath. In another embodiment, the sheath encloses the helical lattice of the thrombectomy device, thereby maintaining or constraining the thrombectomy device in the compressed state. In some embodiments the shaft is enclosed within the sheath (e.g., within the lumen of the sheath).

In some embodiments, the system is configured so that negative pressure (e.g., vacuum pressure) can be applied through the one or more inlet ports. In some embodiments, the one or more inlet ports are located within the housing at the proximal end of the shaft and are in fluid communication with the sheath surrounding the shaft. In other embodiments, the one or more inlet ports are configured such that a fluid or positive or negative pressure can be translated from the one or more inlet ports to the distal end of the shaft and/or at or near the proximal end of the thrombectomy device. In some embodiments, the one or more inlet ports are configured to facilitate infusion of a therapeutic agent (e.g., one or more of heparin, tPA, nitroglycerin, and calcium channel blockers) through the one or more inlet ports and to the thrombectomy device.

In a third aspect, the disclosure features a method of removing a thrombus from a blood vessel, comprising: a) inserting the thrombectomy device of the first aspect in the compressed state into the blood vessel; b) advancing the thrombectomy device through the blood vessel and into contact with the thrombus b) allowing the thrombectomy device to convert to the uncompressed state (e.g., by moving the sheath away from the helical lattice, thereby releasing and allowing expansion of the helical lattice); and c) retracting the thrombectomy device, thereby removing the thrombus. For example, rotating the helical lattice using the rotary causes engagement with the thrombus and retracting the thrombectomy device promotes removal of the thrombus.

In a fourth aspect, the disclosure features a method of removing a thrombus from a blood vessel, comprising: a) inserting the thrombectomy device of the first aspect in the compressed state into the blood vessel; b) advancing the thrombectomy device through the blood vessel; c) allowing the thrombectomy device to convert to the uncompressed state; and d) rotating the thrombectomy device about the first axis, thereby disrupting or breaking apart the thrombus.

In some embodiments of the third or fourth aspect, the thrombectomy device is present in a delivery system, in which the delivery system includes the thrombectomy device and a housing including one or more of an inlet port, a guidewire, a pusher, a sheath, a deployment mechanism configured to retract the sheath into the body of the housing, and a rotator configured to rotate the thrombectomy device.

In some embodiments of the third or fourth aspect, the method further comprises providing aspiration to the thrombus.

In some embodiments, the thrombectomy device is present in a delivery system that includes the thrombectomy device and one or more of a guidewire, a pusher, and/or a sheath, wherein the sheath may include one or more inlet ports. In some embodiments, the lumen of the sheath encloses the thrombectomy device and maintains or constrains the thrombectomy device (e.g., the helical lattice) in the compressed state. In some embodiments, after step b) and prior to step c), the sheath is retracted. In some embodiments, retracting the sheath includes holding the thrombectomy device in place and pulling back on the sheath.

In some embodiments, advancing the thrombectomy device in the blood vessel of the subject includes positioning the thrombectomy device on the distal end of the thrombus (e.g., the shaft spans the length of the thrombus). In some embodiments, advancing the thrombectomy device in the blood vessel of the subject includes advancing the thrombectomy device along a guidewire. In some embodiments, advancing the thrombectomy device in the blood vessel includes applying a biasing force to the proximal end of the thrombectomy device via the shaft, which directs the thrombectomy device in the proximal direction. In some embodiments, the method includes repositioning the thrombectomy device at any point during the method by applying force to the thrombectomy device through the shaft.

In some embodiments, the method comprises mechanical thrombectomy. In some embodiments, the method comprises rotational thrombectomy.

In some embodiments, the sheath includes a proximal end and a distal end, in which the proximal end comprises the inlet port (e.g., the inlet port includes a tube that fluidly connects the inlet port to the sheath). In some embodiments, the method includes aspirating the thrombus through the sheath by applying negative pressure to the inlet port. In some embodiments, the method includes infusing a therapeutic agent through the inlet port and along sheath, thereby delivering the therapeutic agent to the site of the thrombus. In some embodiments, the therapeutic agent is one or more of heparin, tPA, nitroglycerin, and calcium channel blockers. In some embodiments, the method includes administering a therapeutic agent.

In some embodiments, the lumen of the sheath maintains or constrains the thrombectomy device (e.g., the helical lattice) in the compressed state. In some embodiments, after step b) and prior to step c), the sheath is retracted. In some embodiments, retracting the sheath includes holding the thrombectomy device in place and pulling back on the sheath, thereby deploying thrombectomy device in the blood vessel and allowing the thrombectomy device (e.g., the helical lattice) to assume the uncompressed state. In some embodiments, advancing the thrombectomy device in the blood vessel of the subject comprises advancing the thrombectomy device along a guidewire.

In some embodiments, advancing the thrombectomy device in the blood vessel comprises applying force to the proximal end of the thrombectomy device via the shaft. In some embodiments, the shaft of the thrombectomy device comprises a lumen configured to fit the guidewire, and advancing the thrombectomy device along the guidewire comprises advancing the shaft along the guidewire.

In some embodiments, the method includes repositioning the thrombectomy device by applying force to the thrombectomy device through the shaft. In some embodiments, force is applied to the shaft via the housing.

In some embodiments, the blood vessel is a fistula, a graft, a common carotid artery, an internal carotid artery, a basilar artery, an anterior, middle, or posterior cerebral artery, a coronary artery, a renal artery, or superior mesenteric artery. In some embodiments, the thrombectomy device contacts the wall of the blood vessel in at most 4 locations (e.g., at most 3 locations, at most 2 locations, 1 location). In some embodiments, the thrombectomy device does not contact the wall of the blood vessel.

In a fifth aspect, the disclosure features a kit containing the thrombectomy device of the first aspect and one or more additional components. In some embodiments, the one or more additional components include a catheter, a sheath, or a housing (e.g., a housing at a proximal end of the shaft of the thrombectomy device that includes a hand-held portion that can be gripped by the operator of the thrombectomy device and that can be used to manipulate the thrombectomy device).

Definitions

To facilitate an understanding of this disclosure, a number of terms are defined below. Terms defined herein have meanings as commonly understood by a person of ordinary skill in the areas relevant to the disclosure. Terms such as “a,” “an,” and “the” are not intended to refer to only a singular entity but include the general class of which a specific example can be used for illustration. The terminology herein is used to describe specific embodiments of the disclosure, but their usage does not limit the disclosure, except as outlined in the claims.

As used herein, the term “about” refers to a value that is within 10% above or below the value being described.

As used herein, a “rotational thrombectomy” refers to a method in which a thrombus is physically degraded, reduced in size, or broken down. A rotational thrombectomy may be performed by, e.g, rotating a thrombectomy device about an axis parallel to the blood vessel, thereby breaking down the thrombus and restoring flow through the blood vessel. Rotational thrombectomies may use a rotational velocity of from about 0.5 rpm to about 5000 rpm.

As used herein, “mechanical thrombectomy” refers to a method wherein an occlusion (e.g., a clot or thrombus) is physically removed from a blood vessel. A mechanical thrombectomy may be performed by, e.g., adhering a thrombectomy device to a thrombus by, e.g., physically contacting the thrombus with the thrombectomy device and retracting the thrombectomy device out of the blood vessel, thereby removing the thrombus and restoring flow through the blood vessel.

As used herein, an “occlusion,” refers to any blockage in the vascular system of a subject (e.g., a thrombus, a clot, an embolus, etc.). The blockage may be adhered to an interior wall of a vessel. The blockage may partially or completely restrict blood flow in the vascular system of a subject. The presence of an occlusion (e.g., a thrombus) in the vascular system of a subject may reduce blood flow to a value lower than a healthy subject would experience in the same artery or vein (e.g., an artery or vein lacking the occlusion). For a vein, for example, the blood flow may be reduced to less than 30 mL/s, less than 15 mL/s, less than 5 mL/s, less than 1 mL/s, less than 0.5 mL/s, less than 0.1 mL/s, less than 0.05 mL/s, less than 0.04 mL/s, less than 0.03 mL/s, less than 0.02 mL/s, less than 0.01 mL/s, or to about 0 mL/s.

By “treating” or “treatment” is meant the medical management of a subject with the intent that an amelioration, repair, or prevention of a further injury, disease, pathological condition, or disorder will result. Exemplary injuries, diseases, pathological conditions, or disorders include: thrombosis (including arterial thrombosis, venous thrombosis, and deep vein thrombosis, pulmonary embolisms, and arterial thrombosis), antiphospholipid antibody syndrome, prothrombin gene mutation, Factor V leiden mutation, protein deficiency (e.g., Protein C, Protein S, or ATIII, etc.), strokes, heart attacks, limb loss from amputation, paralysis, hormone imbalances (e.g., increased estrogen), compression from other organs and/or tumors on the vessel, sustained veinous damage as a result of frequent veinous access, or as a result of forming a fistula or graft. Additionally, the injury, disease, or disorder may be a result of prior medical treatment for an injury, disease, or disorder requiring treatment with, e.g., hormone therapy, antifibrinolytic drugs (e.g., aprotinin, tranexamic acid, etc.), chemotherapy drugs (e.g., cisplatin and tamoxifen), or endovascular procedures (e.g., angioplasty, atherectomy, stent removal, vein embolization, etc). Treatment or treating includes partial or complete removal of an occlusion (e.g., a thrombus) before the subject experiences further damaging health effects resulting from the occlusion, e.g., reduced blood flow causing a myocardial infarction or stroke. Treating or treatment may further include application of a chemical composition which aids in removal of the occlusion and/or prevents a further occlusion from forming. Treating and treatment include: active treatment, that is, treatment directed specifically toward improvement of the injury or disease, pathological condition, or disorder, and also includes causal treatment, that is, treatment directed toward removal of the cause of the injury or disease, pathological condition, or disorder. In addition, this term includes palliative treatment, that is, treatment designed for the relief of symptoms rather than the curing of the injury or disease, pathological condition, or disorder; preventive treatment, that is, treatment directed to prevention of the injury or disease, pathological condition, or disorder; and supportive treatment, that is, treatment employed to supplement another specific therapy directed toward the improvement of the injury or disease, pathological condition, or disorder.

By "vessel" is meant any circulatory conduit in a subject, including but not limited to aorta, arteries, arterioles, capillaries, veins, fistulas, grafts, and stents.

As used herein, any values provided in a range of values include both the upper and lower bounds, and any values contained within the upper and lower bounds.

BRIEF DESCRIPTION OF THE DRAWINGS

The following detailed description of the embodiments of the disclosure may be better understood when read in conjunction with the appended drawings. It should be understood, however, that the disclosure is not limited to the precise arrangement and instrumentalities of the embodiments shown in the drawings.

FIG. 1A shows a side-on view of the device, highlighting proximal end 110 and distal end 120 of thrombectomy device 100. FIGS. 1B-1F show rotation of the device about the z-axis assigned in FIG. 1A.

FIG. 7A is an image showing delivery device 200 including housing 210, sheath 220, and deployment mechanism 230. FIG. 7B is an image showing shaft 170 and thrombectomy device 100 compressed within sheath 220. FIG. 7C is an image showing thrombectomy device 100 after sheath 220 has been retracted (e.g., by deployment mechanism 230), allowing thrombectomy device 100 to expand to the uncompressed state.

FIG. 8A is an image showing an external view of housing 210 including shaft 170, reinforced region 211, deployment mechanism 230, rotary actuator 240, and inlet port 250. FIG. 8B is a schematic showing the interior of housing 210, including shaft 170, reinforced region 211, deployment mechanism 230, rotary actuator 240, and rotator 241 including and optional motor 242 and gear 243.

FIG. 9A is an image showing thrombectomy device 100 before sheath 220 is retracted. FIGS. 9B-9D are images showing the gradual expansion release of helical lattice 130 of thrombectomy device 100 as sheath 220 is retracted by operation of deployment mechanism 230.

DETAILED DESCRIPTION

The present disclosure, in general terms, features devices, systems, methods, and kits for removing an occlusion (e.g., a blood clot or thrombus) in a blood vessel, e.g., for performing a thrombectomy. In particular, the present disclosure features a thrombectomy device for clearing blood clots, e.g., from hemodialysis access circuits including Arteriovenous Fistulas (AVFs) and Arteriovenous Grafts (AVGs). The device can be a rotational thrombectomy device, which can be used to break up the blood clot into smaller pieces. Alternatively, the thrombectomy device can be a mechanical thrombectomy device, which can be used to remove blood clots from an artery or vein, most often arteries in the brain, heart, or another end organ.

Figure 1A:
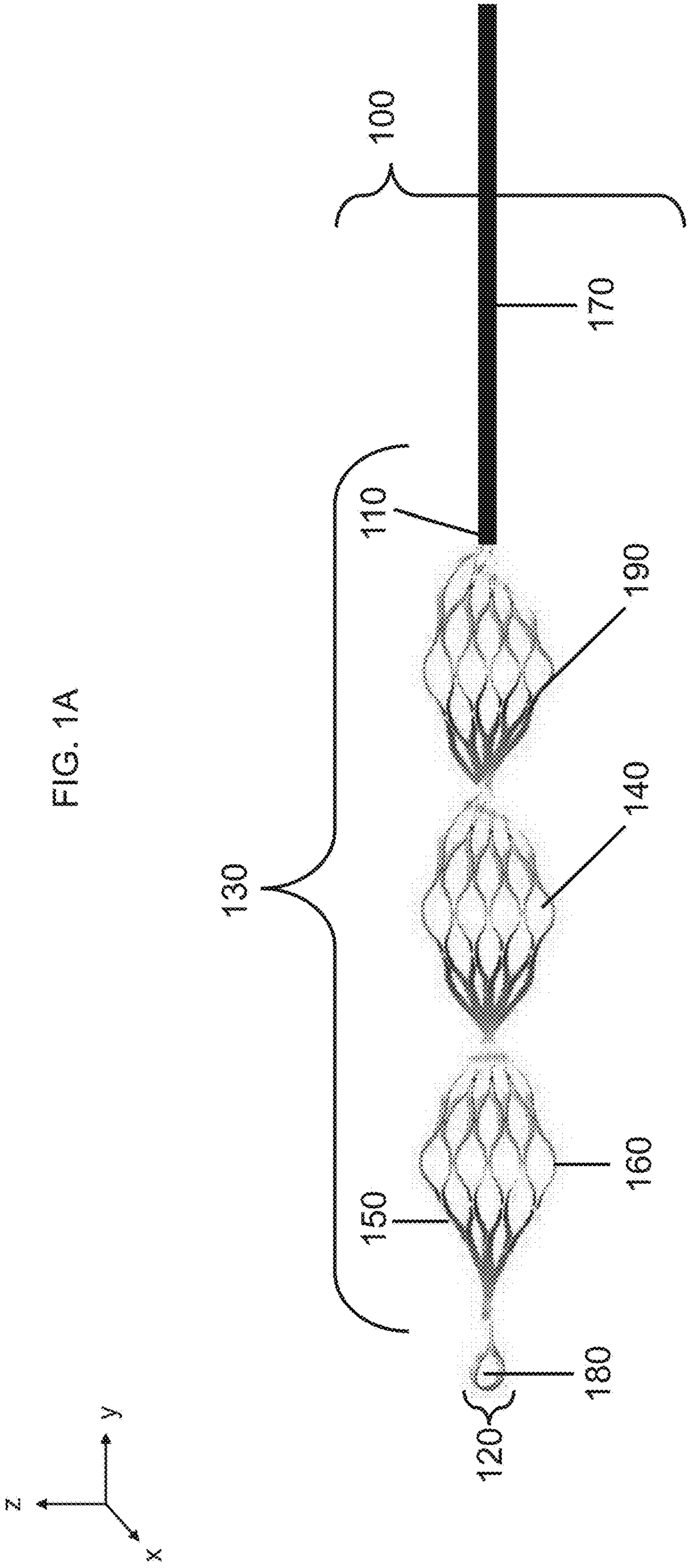
FIGS. 1A-1F are images showing an embodiment of thrombectomy device 100 including proximal end 110, distal end 120, and helical lattice 130 including lattice cells 140 therebetween, as well as shaft 170 and distal connector 180. The device may include coating 190. Each figure includes a common axis system highlighting the relative orientation of the exemplary device in each figure.
Figure 1B:
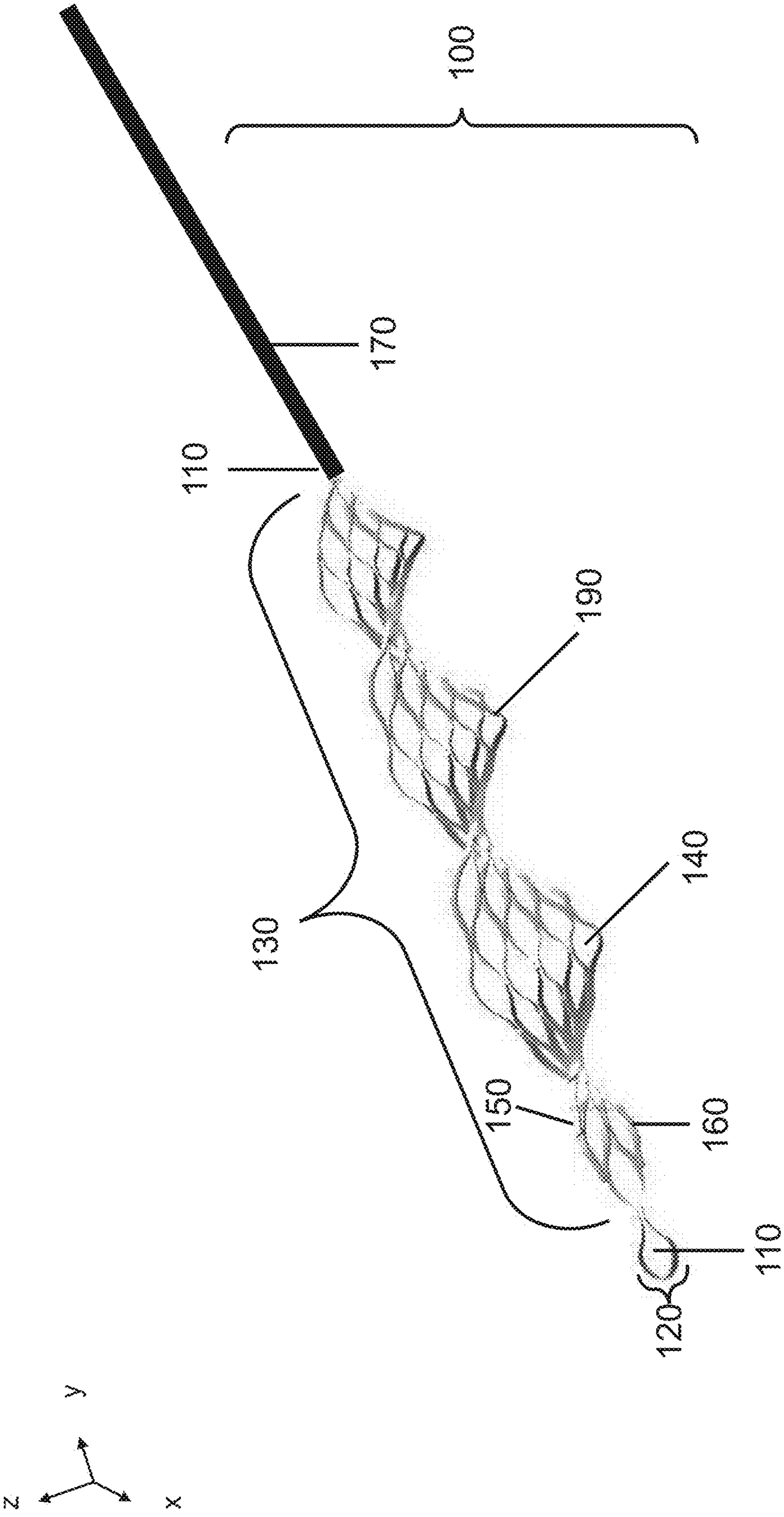
Figure 1C:
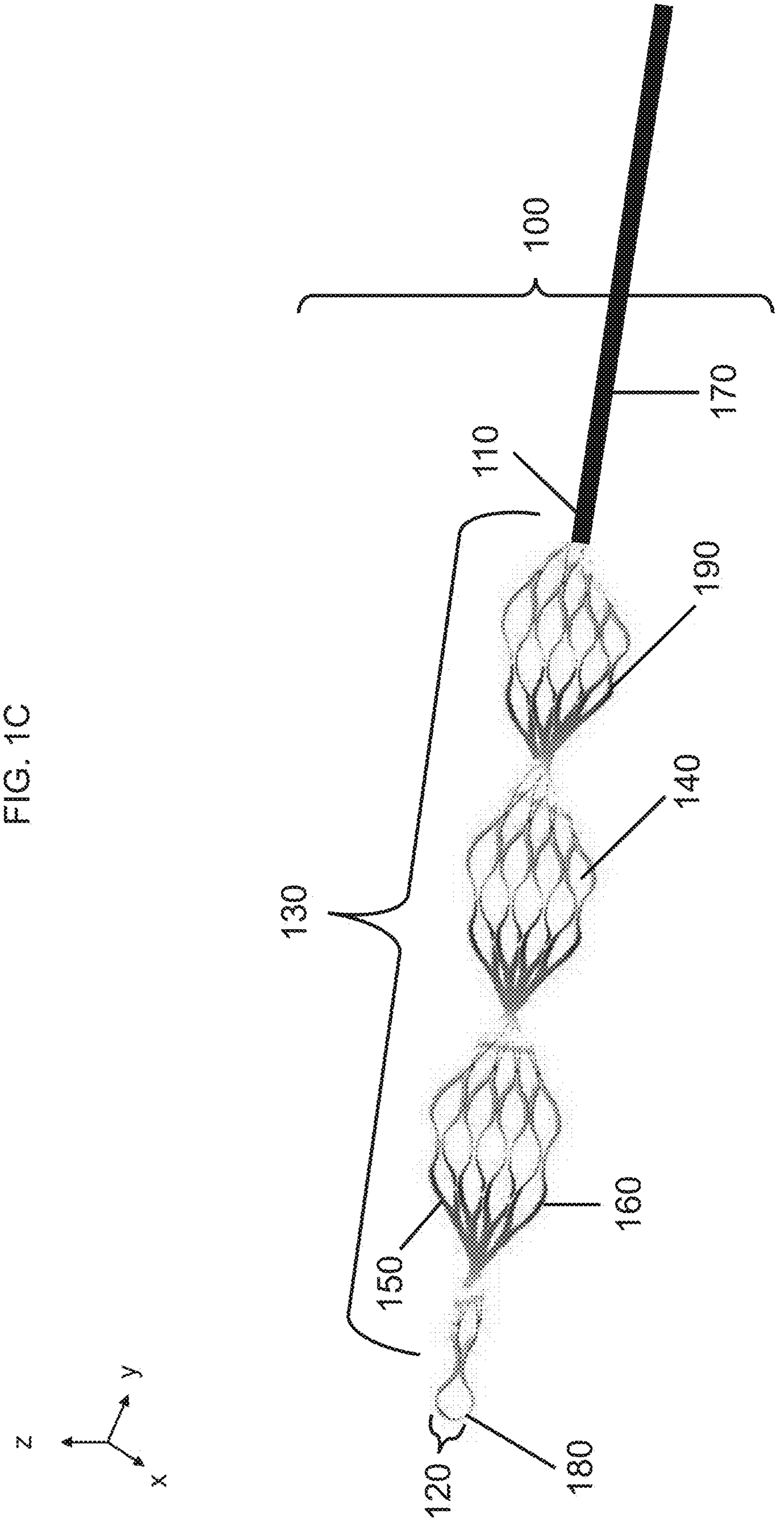
Figure 1D:
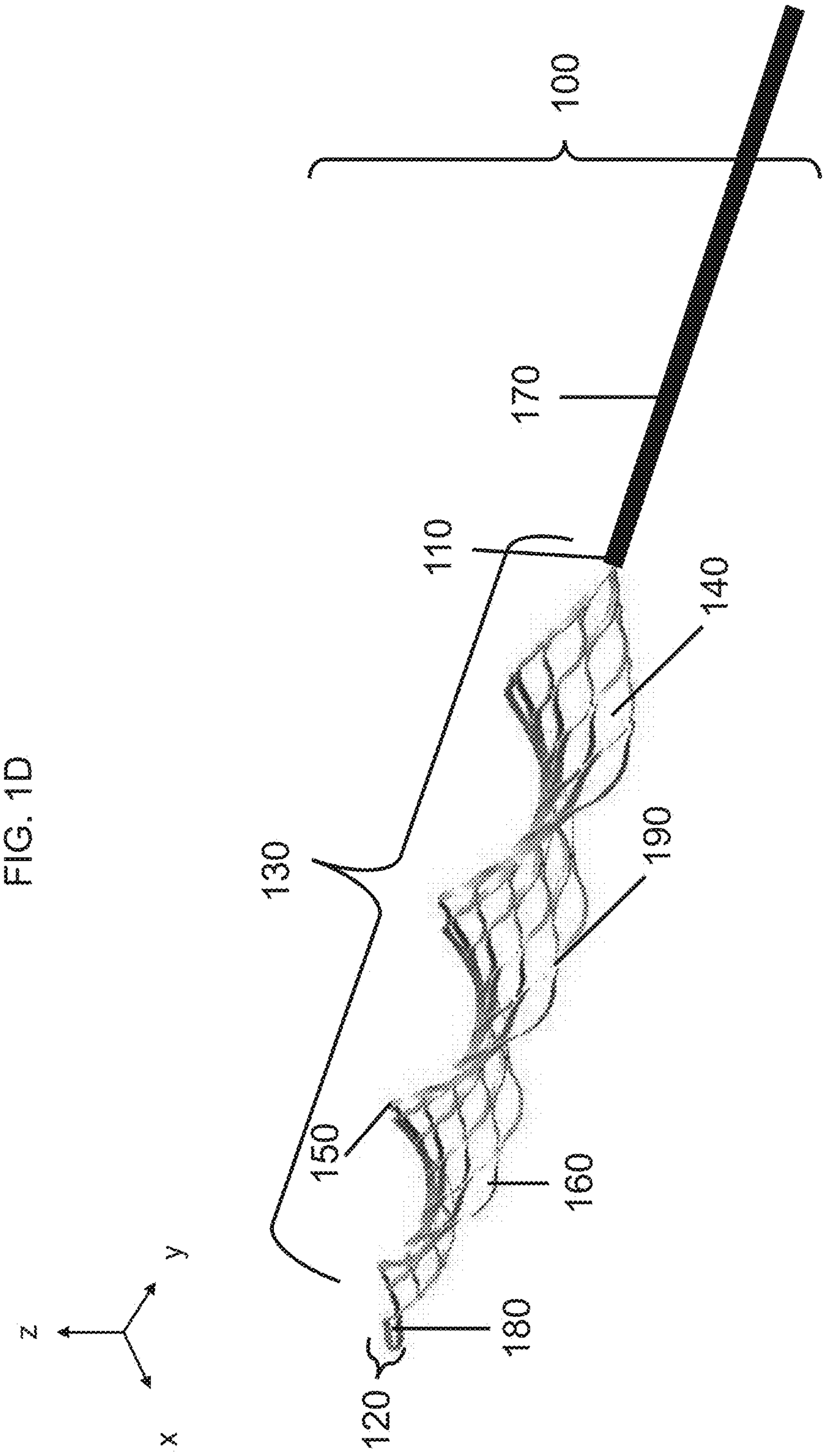
Figure 1E:
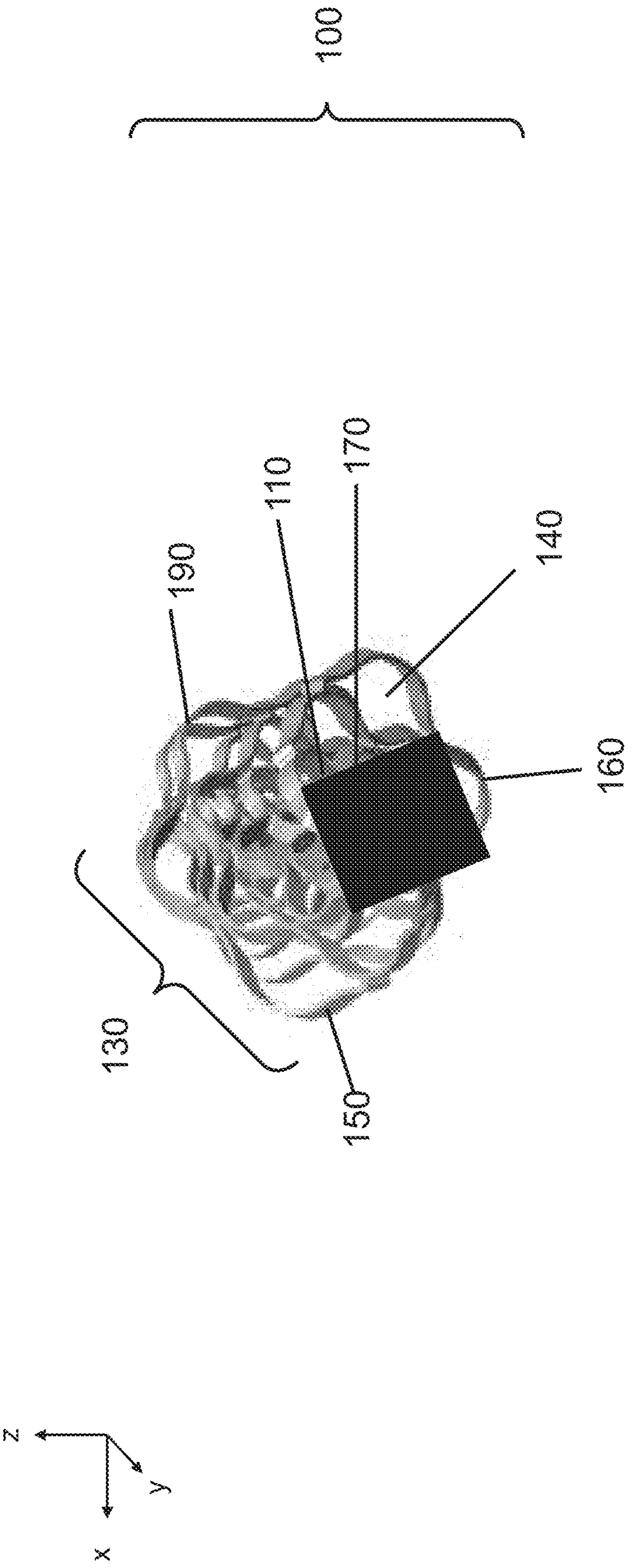
Figure 1F:
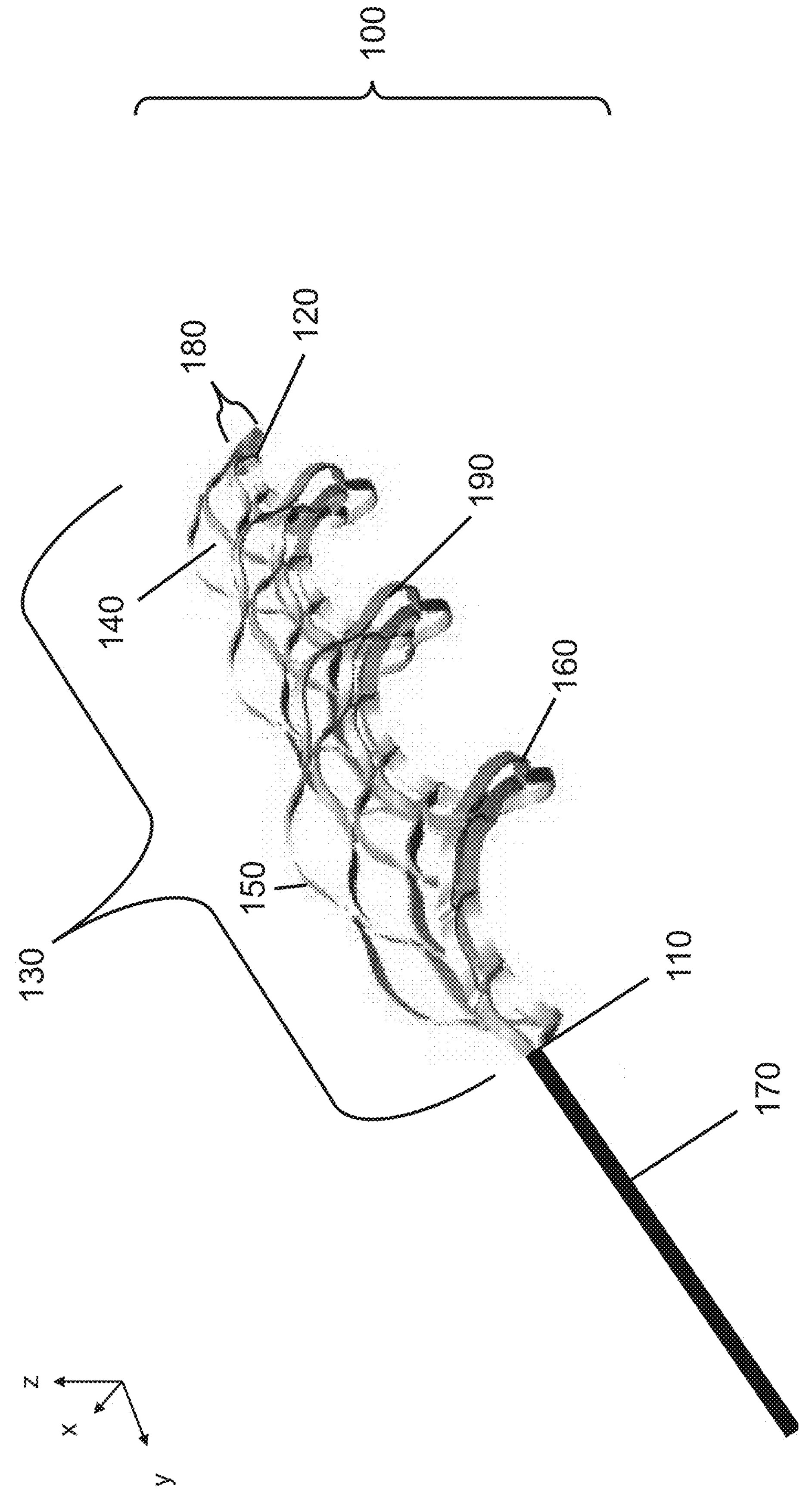
Figure 5:
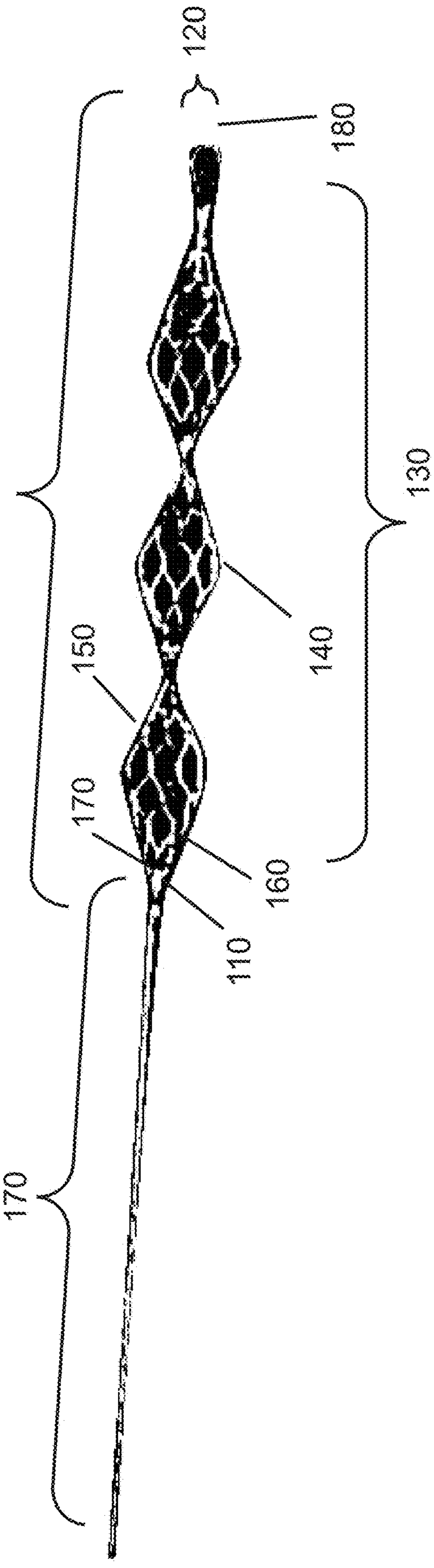
FIG. 5 is an image of thrombectomy device 100 and including shaft 170.

FIG. 1A shows a side view of thrombectomy device 100. FIG. 1B-1F show different orientations of thrombectomy device 100 after rotation about an axis. Thrombectomy device 100 includes a proximal portion, a distal portion, and a middle portion, all of which are disposed between proximal end 110 and distal end 120. The middle portion of the device includes helical lattice 130, which is made of a network of lattice cells 140 therebetween. Helical lattice 130 may include first outer edge 150 and second outer edge 160, and disposed therebetween is the network of lattice cells 140. Proximal end 110 may further include a shaft 170 (See, e.g., FIG. 5). Shaft 170 may be fixedly connected to helical lattice 130. Shaft 170 may be attached to helical lattice 130 at proximal end 110 and/or distal end 120, or a portion thereof. Distal end 120 may further include distal connector 180. If desired, shaft 170 may be reversibly joined to thrombectomy device 100 (e.g., by using a hook and loop connection, an attraction force (e.g., a magnet), or other connection, e.g., at proximal end 110) in order to switch out the thrombectomy device for one having a different dimension.

Figure 2:
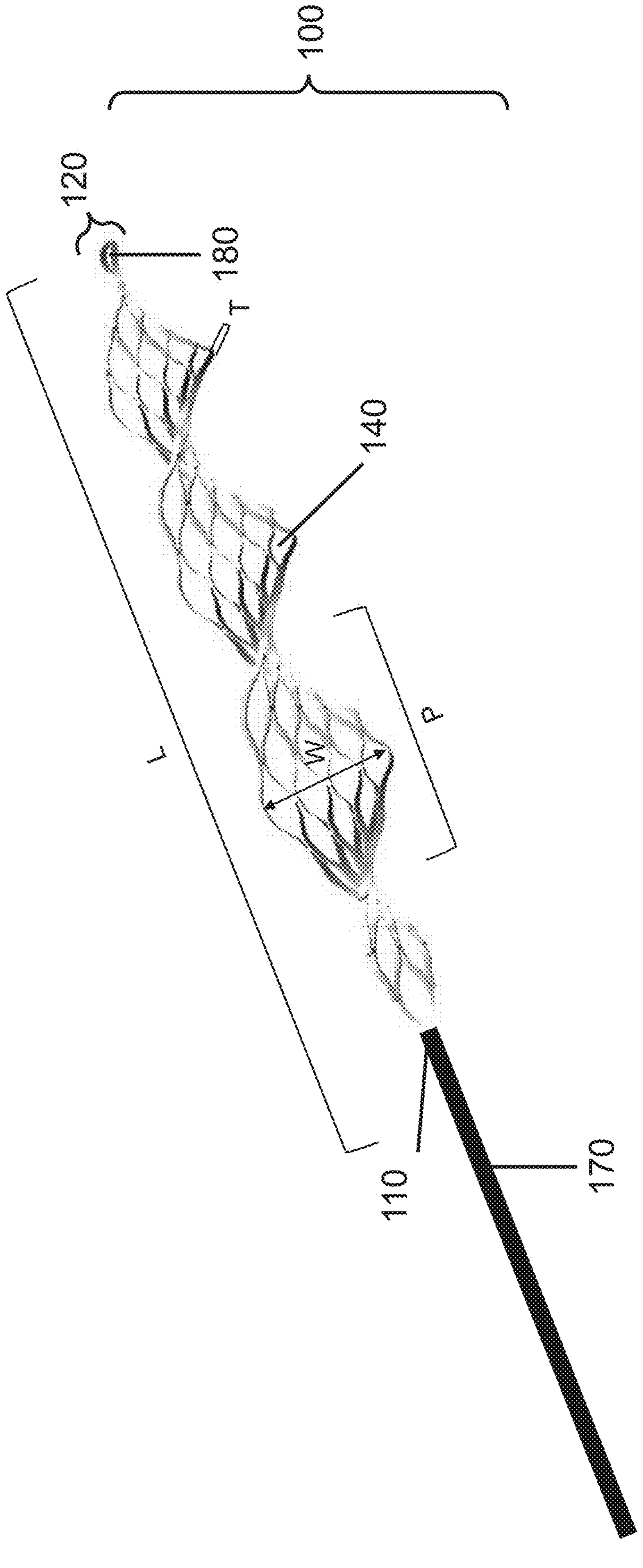
FIG. 2 is an image of a thrombectomy device labeled to define the length (L), width (W), and thickness (T) of the thrombectomy device, as well as the pitch (P) of a turn of the helical lattice.

Thrombectomy device 100 is defined by a length (L) and width (W) (FIG. 2). The length of thrombectomy device 100 is the distance along a first axis, defined as the distance between proximal end 110 and distal end 120. The length of thrombectomy device 100 may be from about 10 mm to about 600 mm (e.g., from about 20 mm to about 500 mm, from about 30 mm to about 400 mm, from about 40 mm to about 300 mm, from about 50 mm to about 200 mm, from about 60 mm to about 100 mm, about 80 mm, etc.). The width of the thrombectomy device is the distance between two points on the thrombectomy device along a second axis perpendicular to the first axis. The width or thickness of the device may be constant along the length of the device, or it may vary. The width of thrombectomy device 100 may be from about 1 mm to about 30 mm (e.g., from about 1 mm to about 20 mm, from about 5 mm to about 20 mm, from about 5 mm to about 15 mm. etc.).

Proximal end 110 and distal end 120 may both be fixedly attached to shaft 170. The proximal portion of thrombectomy device 100 includes proximal end 110 and shaft 170. Shaft 170 may be fixedly attached to proximal end 110 and/or distal end 120. For example, first outer edge 150 and second outer edge 160 may be fixedly attached to shaft 170 at proximal end 110. Shaft 170 may then extend along the middle portion of thrombectomy device 100 which includes helical lattice 130 past distal end 120. First outer edge 150 and second outer edge 160 may both be fixedly attached to shaft 170 at distal end 120. Shaft 170 may include a lumen spanning the length of shaft 170, wherein the lumen is sized to fit over a guidewire.

The middle portion of thrombectomy device 100, which includes helical lattice 130 may have a length from about 10 mm to about 600 mm and a width from about 1 mm to about 30 mm (e.g., from about 1 mm to about 20 mm, from about 5 mm to about 20 mm, from about 5 mm to about 15 mm. etc.). The width of the middle portion may be periodic along its length. Distal connector 180 may be conical. When conical, distal connector 180 has a radius of from about 0.1 to 2.5 mm at the widest point and a length of from about 0.5 mm to about 5 mm. The helical lattice may have a width greater than the width of either shaft 170 or distal connector 180.

Shaft 170 has a length that is sufficient to navigate the vasculature of the subject, from an entry point to the site of the occlusion (e.g., a thrombus). Shaft 170 may extend through the helical lattice of the thrombectomy device.

All or a portion of thrombectomy device 100, e.g., helical lattice 130, can include a shape memory material. The shape memory material may be or may include nitinol, stainless steel, or a shape memory polymer (see, e.g., US 2011/0039967, U.S. Pat. Nos. 9,745,402, and 11,453,740, each of which is incorporated herein by reference). Thrombectomy device 100 may be made of more than one material. Proximal end 110 and distal end 120 may independently be made out of a material with a Young's Modulus of at least 28 GPa (e.g., a Young's Modulus within the range of about 10 to about 50 GPa). Any portion of thrombectomy device 100 may be reinforced with a reinforcement material. For example, a connection between shaft 170 and helical lattice 130 (e.g., at proximal end 110) may be reinforced with a reinforcement material. The reinforcement material may be a wire, a braid, or a coil through or within proximal end 110. The reinforcement material may be a continuous layer on the surface of proximal end 110. Additionally, any region which may be sensitive to stress (e.g., a region connecting any two components, e.g., sheath 220 and housing 210, shaft 170 and housing 210) may be reinforced with a reinforcement material. For example, housing 210 may include reinforced region 211 which reduces the strain on the connection between shaft 170 and housing 210, sheath 220 and housing 210, or both. Proximal end 110 and distal end 120 may independently be made out of a flexible material (e.g., a silicone rubber). Proximal end 110 may be fixedly attached to shaft 170.

Helical lattice 130 includes one or more turns along the first axis of the thrombectomy device (e.g., 1 to 10 turns, from 1 to 5 turns, or 3 turns). Each turn is defined by a pitch (P). The pitch of the helical lattice may be from 1 mm to 30 mm (e.g., about 1 mm to about 20 mm, about 5 mm to about 20 mm, or about 5 mm to 15 mm, etc.). The pitch of each turn may be the same or different. Helical lattice 130 further includes several lattice cells 140, each of which is defined by a shape and an area. The shape and/or area of all lattice cells 140 of helical lattice 130 may be identical. The shape and/or area of one or more lattice cells 140 may be different than one or more other lattice cells 140 of helical lattice 130. Helical lattice 130 may include more than one, e.g., more than two, more than three, more than four, more than five, more than six, more than seven, more than eight, more than nine, more than ten, etc., different shapes and/or areas of lattice cells 140.

A person skilled in the art may choose a thrombectomy device of appropriate length, width, thickness, number of turns, pitch of the one or more turns, shape of the lattice cell, and/or area of the lattice cell for the removal of a thrombus. A person of skill in the art may chose the dimensions of a thrombectomy device based on, e.g., the size of the vessel (see Table 1), the flow of blood through and around the vessel (e.g., the vessel tortuosity), and/or the chronicity (i.e., age) of the clot (e.g., less than 2 weeks, between 2 weeks and 8 weeks, greater than 8 weeks, etc.).

Thrombectomy device 100 can be sized to fit inside a selected blood vessel. The length or width of the device may be varied to be slightly smaller (e.g., from about 1% to about 99% of the length or width of the blood vessel, about 10% to about 90% of the length or width of the blood vessel, about 20% to about 80% of the length or width of the blood vessel, about 30% to about 70% of the length or width of the blood vessel, about 40% to about 60% of the length or width of the blood vessel, or about 50% of the length or width of the blood vessel). For example, thrombectomy device 100 can be provided in any of a number of different sizes that are configured to fit within a target blood vessel. Examples of vessels and their sizes are provided in Table 1.

TABLE 1

| Vessel | Diameter |
|---|---|
| Aorta | 2 cm to 3 cm |
| Vein | 0.6 cm to 1.2 cm |
| Artery | 3 mm to 25 mm |
| Graft | About 6 mm |
| Stent | 2.5 to 4 mm |
| Arteriole | 7 μm to about 100 μm |
| Capillary | 2 μm to 12 μm |
| Fistula | 0.5 cm to 2.5 cm |

Examples of blood vessels in which thrombectomy device 100 may be used include a fistula, a graft, a common carotid artery, an internal carotid artery, a basilar artery, a middle, anterior, or posterior cerebral artery, a coronary artery, a renal artery, or the superior mesenteric artery.

Thrombectomy device 100 may be sized to fit within, for example, an aorta, an artery, an arteriole, capillaries, a vein, a fistula, a graft, a stent, and any other vessels described herein. Thrombectomy device 100 may be sized to have limited contact with vessel wall (e.g., less than 5 points of contact, less than 4 points of contact, less than 3 points of contact, less than 2 points of contact, or does not substantially contact the vessel wall (e.g., has a width that is narrower than the width of a target vessel at the site of an occlusion, such as a thrombus)).

Thrombectomy device 100 can adopt a first state (the uncompressed state or the non-distorted state) and can be deformed to a second state (compressed state or the distorted state). In the uncompressed state, thrombectomy device 100 can have a width from about 1 mm to about 30 mm. In the compressed state, thrombectomy device 100 can have a width from about 0.5 mm to about 6 mm (see FIG. 3). A thrombectomy device may be selected that has a width that is greater than the width of the occluded vessel. In this case, the compressed thrombectomy device, once unsheathed, would decompress to the uncompressed state. Said expansion may be expansion into the uncompressed state (e.g., the device would expand to rest against the vessel wall) or a partially uncompressed state. The partially uncompressed state may have a width greater than the width of the compressed state (e.g., greater than about 0.5 mm), and less than the uncompressed state (e.g., less than about 30 mm).

The width of thrombectomy device 100 in the compressed state, uncompressed state, or both may be variable along the length. Thrombectomy device 100 can be deformed into the compressed state upon loading into sheath 220 (or other material capable of constraining the shape of thrombectomy device 100) of delivery system 200. Thrombectomy device 100 may then be guided to the site of the occlusion (e.g., a thrombus) by delivery system 200. Once navigated to the site of the occlusion, thrombectomy device 100 may then be deployed (e.g., allowed to expand, removed from sheath 220, etc.)

Figure 3:
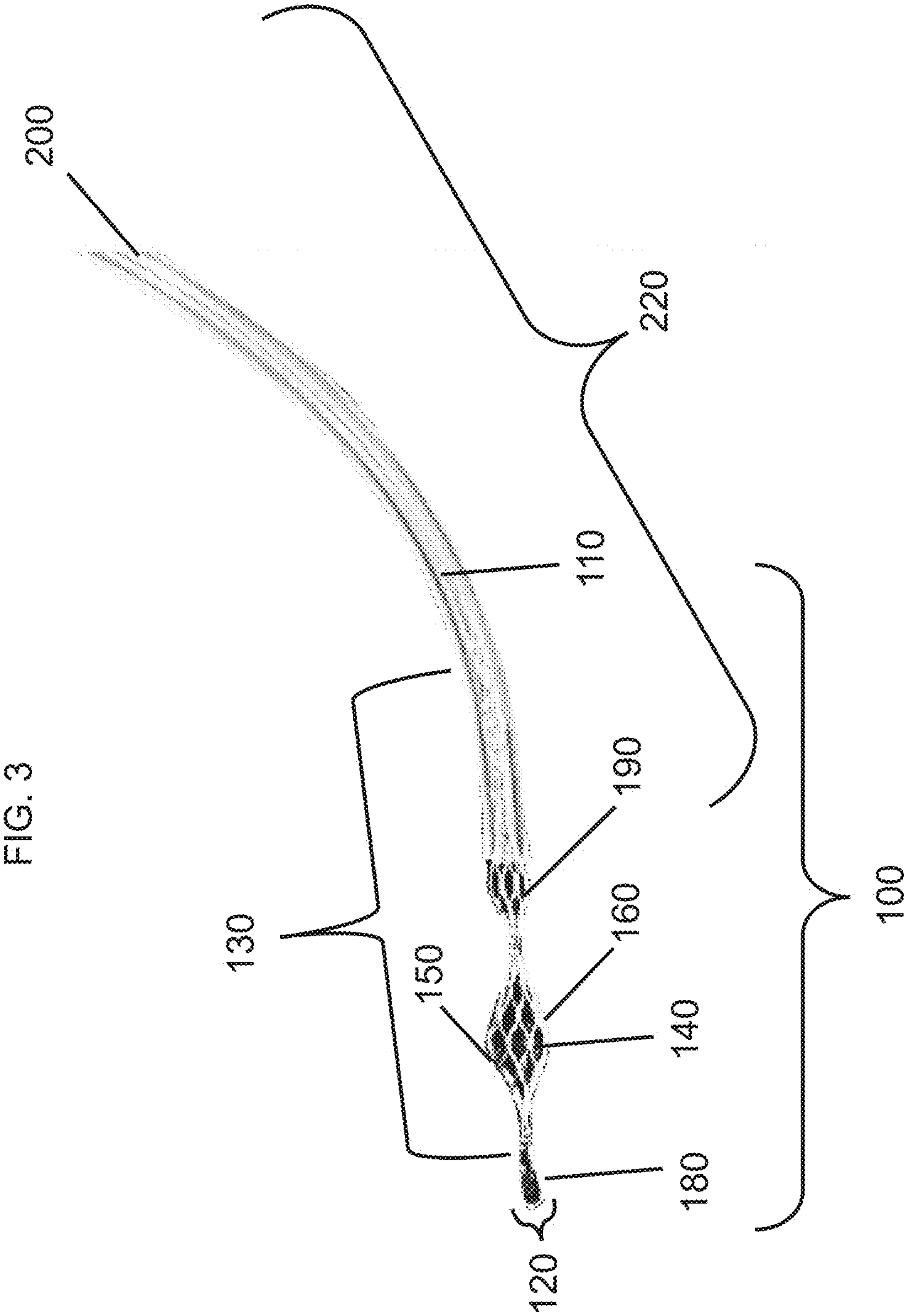
FIG. 3 is an image of thrombectomy device 100 partially inserted into delivery system 200, which includes sheath 220. Proximal end 110 of thrombectomy device 100, shaft 170, and a portion of helical lattice 130 are compressed inside sheath 220. Distal end 120, distal connector 180, and a portion of helical lattice 130 are uncompressed outside of sheath 220.
Figure 4:
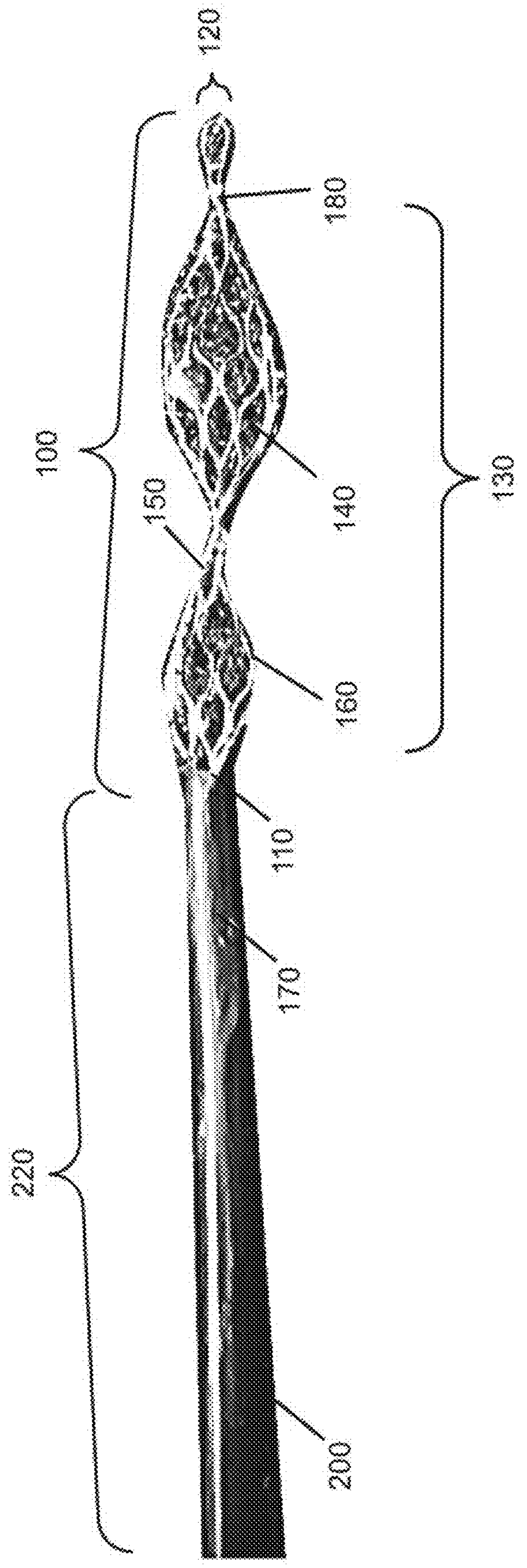
FIG. 4 is an image of thrombectomy device 100 partially inserted into delivery system 200, which includes sheath 220. Shaft 170 is fully contained in sheath 220.

Thrombectomy device 100 may be included in a delivery system 200 including thrombectomy device 100 and one or more additional components (see, e.g., FIG. 3). Delivery system 200 may include housing 210, sheath 220 (including proximal end 221 and distal end 222), deployment mechanism 230, rotary actuator 240, and/or inlet port 250. Housing 210 may be connected to, e.g., sheath 220, deployment mechanism 230, rotary actuator 240, and/or shaft 170. For example, deployment mechanism 230 and rotary actuator 240 may be located on housing 210, and proximal end of sheath 220 and/or proximal end of shaft 170 may be connected to housing 210. Housing 210 may be sized so as to be held in the hands of an operator during a thrombectomy procedure. Housing 210 may act on shaft 170 such that shaft 170 serves as a pusher of delivery system 200. For example, shaft 170 may be mechanically and/or electronically coupled to the housing, such that advancing the housing advances thrombectomy device 100 through the vasculature of the subject. Housing 210 may include a means of relieving strain on shaft 170, sheath 220, or the guidewire, e.g., by preventing a high-strain bending of shaft 170, sheath 220, or the guidewire. For example, housing 210 may include reinforced region 211.

Sheath 220 may envelope one or more of the thrombectomy device 100 and shaft 170. Sheath 220 may envelope all or a portion of shaft 170. Sheath 220 may be mechanically or electronically coupled to deployment mechanism 230. Deployment mechanism 230 is configured such that operation of deployment mechanism 230 manipulates sheath 220, e.g., retracting sheath 220 or extending sheath 220. For example, prior to deployment of thrombectomy device 100, sheath 220 envelopes thrombectomy device 100, including helical lattice 130 and sheath 170. Operating deployment mechanism 220 retracts sheath 220 thereby releasing helical lattice 130 of thrombectomy device 100 and allowing lattice cells 150 of thrombectomy device 100 to expand from the compressed state to the uncompressed state.

The system may also include a guidewire that can be used to navigate thrombectomy device 100 to a target site in a blood vessel. Shaft 170 may include a lumen spanning the length of shaft 170. When shaft 170 includes a lumen, the lumen may be sized to fit over the guidewire.

Rotary actuator 240 may be mechanically or electronically coupled to rotator 241. Rotator 241 is configured to rotate shaft 170 and/or the guidewire, thereby rotating thrombectomy device 100 (e.g., rotation about the first axis). Rotator 241 may include a motor 242 mechanically coupled to one or more gears 243 in contact with shaft 170. Rotator 241 may rotate thrombectomy device 100 at a rate from about 0.5 rpm to about 5000 rpm. The rate of rotation may be constant, or it may be variable and adjusted by the operator, as needed, during a thrombectomy procedure.

Helical Lattice

As shown in FIGS. 1A-1F, thrombectomy device 100 includes a middle portion with helical lattice 130. Helical lattice 130 includes network of helical cells 140. Helical lattice 130 of thrombectomy device 100 can include about 1 to about 10 turns (e.g., 1, 2, 3, 4, 5, 6 7 8, 9, or 10 turns). Each turn is defined by a pitch P, being the length along the first axis of thrombectomy device 100 for helical lattice 130 to complete a single 360° rotation. Each turn may be of the same pitch or may have a different pitch. For example, each turn may have the same pitch of from about 1 mm to about 30 mm (e.g., 1 mm to about 30 mm (e.g., about 1 mm to about 20 mm, about 5 mm to about 20 mm, or about 5 mm to 15 mm, etc.), or the pitch for each turn may be independently selected from this range (see FIG. 2).

Helical lattice cells 140 are compressible and may be formed in any of a number of different shapes, such as a polygonal, square, rectangular, triangular, diamond, circular, elliptical, oval, oblong, lens, asteroid, deltoid, slit, or amorphous shape. The shape and/or area of all lattice cells 140 of helical lattice 130 may be identical. The shape and/or area of one or more lattice cells 140 may be different than one or more other lattice cells 140 of helical lattice 130. Helical lattice 130 may include more than one, e.g., more than two, more than three, more than four, more than five, more than six, more than seven, more than eight, more than nine, more than ten, etc., different shapes and/or areas of lattice cells 140. Different shapes and/or areas of lattice cells 140 may be chosen to change the flexibility of thrombectomy device 100, compressibility of thrombectomy device 100, or points of contact between thrombectomy device 100 a thrombus. A thrombectomy device of different shapes and/or areas of lattice cells may be chosen by an operator based on, e.g., the location of the thrombus or the chronicity of the thrombus.

Helical lattice 130 may include first outer edge 150 and second outer edge 160, and disposed between is network of lattice cells 140. First outer edge 150 and second outer edge 160 may join to form a structure, e.g., shaft 170 and distal connector 180, at the proximal and distal ends, respectively.

Helical lattice 130 can be constrained in the compressed state by being pulled into sheath 220. Helical lattice 130 may then be navigated to the site of a thrombus by the delivery system 200 (e.g., by applying force to helical lattice 130 via shaft 170, both enclosed in the lumen of sheath 220). Helical lattice 130 may then be released (e.g., deployed) from distal end 222 of sheath 220, which removes the constraint and allows the device to convert to the uncompressed state (e.g., the non-deformed or non-compacted shape; see FIG. 3). Helical lattice may partially expand into a partially uncompressed state, e.g., if a helical lattice is selected which is slightly larger than the vessel the thrombus is in.

Helical lattice 130 includes a length defined along the first axis. The length of helical lattice 130 may be from about 10 mm to about 600 mm (e.g., from about 20 mm to about 500 mm, from about 30 mm to about 400 mm, from about 40 mm to about 300 mm, from about 50 mm to about 200 mm, from about 60 mm to about 100 mm, about 80 mm, etc.). Helical lattice 130 includes a width defined along the second axis. The width is from about 1 mm to about 30 mm when thrombectomy device 100 is in the uncompressed state (e.g., about 1 mm to about 20 mm, about 5 mm to about 20 mm, or about 5 mm to 15 mm, etc.) and from about 0.5 mm to about 6 mm in the compressed state. The width of helical lattice 130 in an uncompressed state may be periodic along the length. Helical lattice 130 can have a thickness of from about 0.01 mm to about 1 mm (see FIG. 2).

Helical lattice 130 may further include a texture (e.g., bumps, dimples, ridges, etc.). Textures may be located on the inner or outer surface of helical lattice 130.

Shafts and Connectors

Thrombectomy device 100 may include shaft 170 and/or distal connector 180. Shaft 170 may be an elongated cylinder. Distal connector 180 may be circular, semicircular, ovoid, cylindrical, or a hook. Shaft 170 may be fixedly connected to helical lattice 130, or a portion of proximal end 110. The shaft may serve to force thrombectomy device 100 through the vasculature of the subject (e.g., by acting as a pusher that can be used to apply a biasing force). Shaft 170 may include a length from about 1 cm to about 200 cm (e.g., from about 20 cm to about 175 cm, from about 30 cm to about 150 cm, from about 40 cm to about 125 cm, from about 50 cm to about 100 cm, about 75 cm, etc.)

Thrombectomy device 100 may be positioned or moved by applying force through shaft 170 at any point during operation. During a mechanical thrombectomy, sheath 220 may be engaged or retracted (e.g., manually or by deployment mechanism 230) in order to facilitate removal of an occlusion (e.g., a thrombus). Deployment mechanism 230 may be used to translate sheath 220 forwards and backwards along shaft 170 (e.g., in a distal direction and in a proximal direction, respectfully, relative to thrombectomy device 100). Engaging deployment mechanism 230 to move sheath 220 in a distal direction can result in the sheathing of thrombectomy device 100 after it has contacted a thrombus, thereby forcing thrombectomy device 100 to adopt the compressed state inside sheath 220, which also pulls the thrombus inside sheath 220, thereby trapping the thrombus.

Shaft 170 may be fixedly attached to helical lattice 130, e.g., at proximal end 110 and/or distal end 120. For example, first outer edge 150 and second outer edge 160 may be fixedly attached to shaft 170 at proximal end 110. Shaft 170 may then extend along the middle portion of thrombectomy device 100 which includes helical lattice 130 past distal end 120. First outer edge 150 and second outer edge 160 may both be fixedly attached to shaft 170 at distal end 120. During a rotational thrombectomy, shaft 170 may be rotated, thereby rotating helical lattice 130 to macerate a thrombus. Shaft 170 may be rotated by, e.g., rotator 241 mechanically or electronically coupled to rotary actuator 240.

Shaft 170 may include a lumen spanning the length of shaft 170, wherein the lumen is sized to fit over a guidewire. The lumen of shaft 170 allows shaft 170 to rotate over the guidewire independent of any rotation of the guidewire, thereby allowing thrombectomy device 100 to macerate a thrombus without any damage to or slippage of the guidewire.

Shaft 170 may be composed of a plurality of segments 171. Each segment 171 is configured such that it may be rotated independently of an adjacent segment (e.g., from 0.01° to 45° relative to an adjacent segment, e.g., from 0.05° to 30°, from 0.1° to 29°, from 0.2° to 28°, from 0.3° to 27°, from 0.4° to 26°, from 0.5° to 25° from 0.6° to 24°, from 0.7° to 23°, from 0.8° to 22°, from 0.9° to 21°, or from 1° to 20°; or at least 0.01°, at least 0.02°, at least 0.03°, at least 0.04°, at least 0.05°, at least 0.06°, at least 0.08°, at least 0.08°, at least 0.09°, at least 0.1°, at least 0.2°, at least 0.3°, at least 0.4°, at least 0.5°, at least 0.6°, at least 0.7°, at least 0.8°, at least 0.9°, at least 1°, at least 2°, at least 3°, at least 4°, at least 5°, at least 6°, at least 7°, at least 8°, at least 9°, at least 10°, at least 15°, at least 20°, at least 25°, at least 30°, at least 35°, at least 40°, or at least) 45°.

Shaft 170 may be composed of a plurality of interconnected segments 171, such as, e.g., at least 10 segments 171 (e.g., at least 20, at least 30, at least 40, at least 50, at least 60, at least 70, at least 80, at least 90, at least 100, at least 150, at least 250, at least 300, at least 350, at least 400, at least 450, at least 500, at least 600, at least 700, at least 800, at least 900, at least 1000, at least 1500, at least 2000, at least 2500, at least 3000, at least 3500, at least 4000, at least 4500, at least 5000, at least 5500, at least 6000, at least 6500, at least 7000, at least 7500, at least 8000, at least 8500, at least 9000, at least 9500, or at least 10000 segments) depending upon the length of shaft 170. Each one of segments 171 may have a length of from about 0.01 mm to about 20 mm (e.g., from about 0.05 mm to 150 mm, from about 0.1 mm to about 100 mm, from about 0.2 mm to about 90 mm, from about 0.3 mm to about 80 mm, from about 0.4 mm to about 70 mm, from about 0.5 mm to about 60 mm, from about 0.6 mm to about 50 mm, from about 0.7 mm to about 40 mm, from about 0.8 mm to about 30 mm, from about 0.9 mm to about 20 mm, or from about 1 mm to about 10 mm); alternatively, each one of segments 171 may have a length of at least about 0.01 mm (e.g., at least about 0.02 mm, at least about 0.03 mm, at least about 0.04 mm, at least about 0.05 mm, at least about 0.06 mm, at least about 0.07 mm, at least about 0.08 mm, at least about 0.09 mm, at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, or at least about 20 mm).

Figure 6:
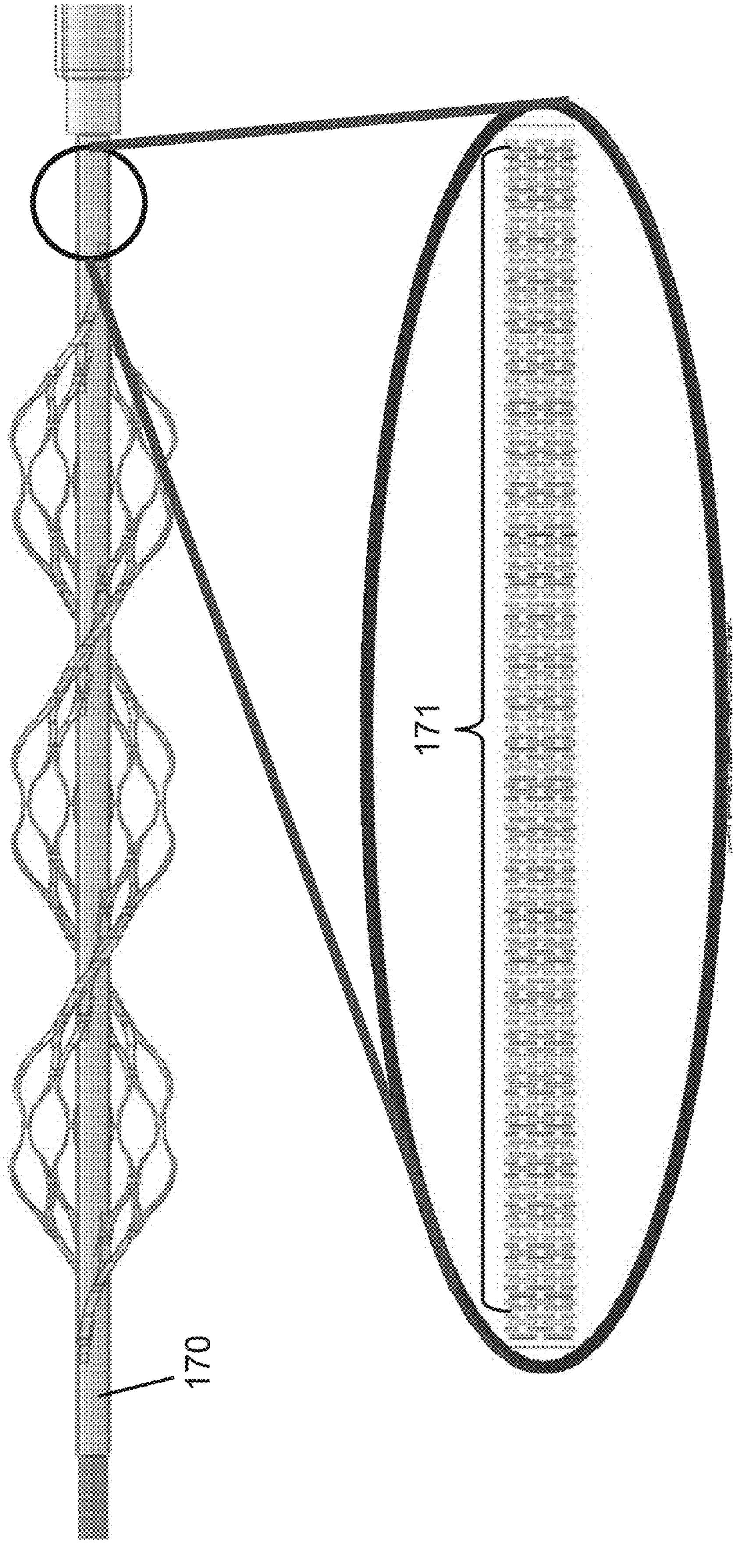
FIG. 6 is an image showing thrombectomy device 100 and an enlarged view of sheath 170 showing a plurality of segments 171 that facilitate the bending flexibility of shaft 170.

Segments 171 may increase the flexibility of shaft 170 relative to a shaft made of an identical material that does not include segments 171 (e.g., a shaft composed of a single piece of a material). The flexibility of shaft 170 may be compared by measuring the flexural modulus (e.g., the maximum stress the material can withstand before failure). The flexural modulus of shaft 170 composed of a plurality of segments 171 may be at least 10 MPa (e.g., at least 20 MPa, at least 30 MPa, at least 40 MPa, at least 50 MPa, at least 60 MPa, at least 70 MPa, at least 80 MPa, at least 90 MPa, at least 100 MPa, at least 150 MPa, at least 200 MPa, at least 300 MPa, at least 350 MPa, at least 400 MPa, at least 450 MPa, at least 500 MPa, at least 550 MPa, at least 600 MPa, at least 650 MPa, at least 700 MPa, at least 750 MPa, at least 800 MPa, at least 850 MPa, at least 900 MPa, at least 950 MPa, or at least 1000 MPa). An example of segments 171 within shaft 170 is shown in FIG. 6.

Distal connector 180, when present, may include a hollow tapered cone or rubber cap that covers the distal end. Alternatively, distal connector 180 may be a blunt end that can be used to interact with a thrombus (e.g., to engage with a clot) during use of thrombectomy device 100. When distal connector 180 is absent, the hollow tapered cone or rubber cap may be present on the distal end of the guidewire.

Coatings

Thrombectomy device 100 may include coating 190 on a surface of the device. Coating 190 includes a compound that can facilitate the removal or breakdown of an occlusion (e.g., a thrombus) or insertion of thrombectomy device 100 into a vessel of a subject. Coating 190 may be a drug, therapeutic agent, lubricant, or adhesive. Coating 190 may be an anticoagulant agent, (e.g., an anti-thrombogenic agent, a blood thinner, a lytic agent (e.g., Reteplase, Alteplase, etc.).

Radiopaque Markers

Thrombectomy device 100 may include a radiopaque marker. Radiopaque markers may be located at, e.g., proximal end 110, distal end 120, along helical lattice 130, etc. Devices combining thrombectomy devices and radiopaque markers are known in the art (see, e.g., U.S. patent application Ser. Nos. 17/168,166; 17/235,764; and 13/827,208, the entire contents of which are incorporated by reference).

Delivery System

Figure 7A:
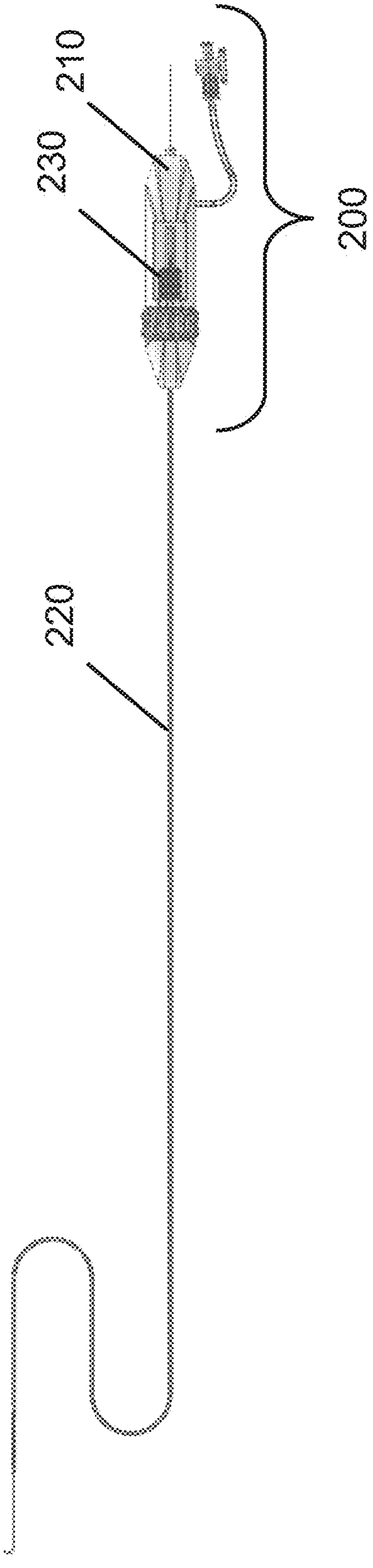
FIGS. 7A-7C is an image showing the connection between thrombectomy device 100 and delivery device 200.
Figure 7B:
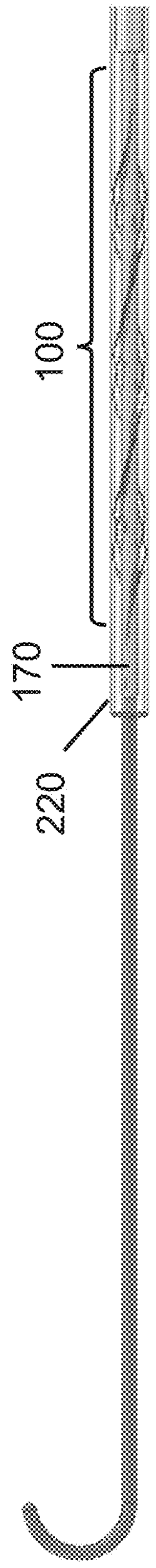
Figure 7C:
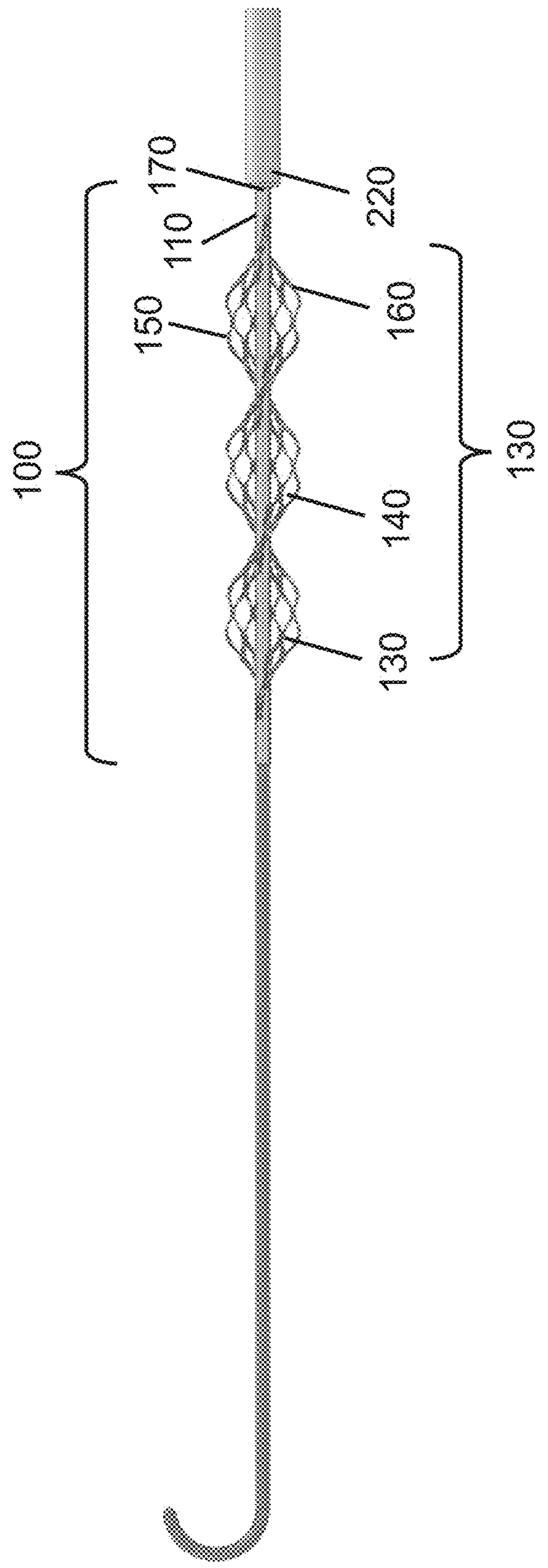

Thrombectomy device 100 may be included with (e.g., as part of a kit) or used in conjunction with (e.g., during a thrombectomy) a delivery system 200. Thrombectomy device 100 interacting with delivery device 200 is shown in FIGS. 7A-7C. Delivery system 200 may be used to navigate thrombectomy device 100 to a desired site in the vasculature of the subject. Delivery system 200 includes housing 210, sheath 220, deployment mechanism 230, rotary actuator 240, and inlet port 250.

Figure 8A:
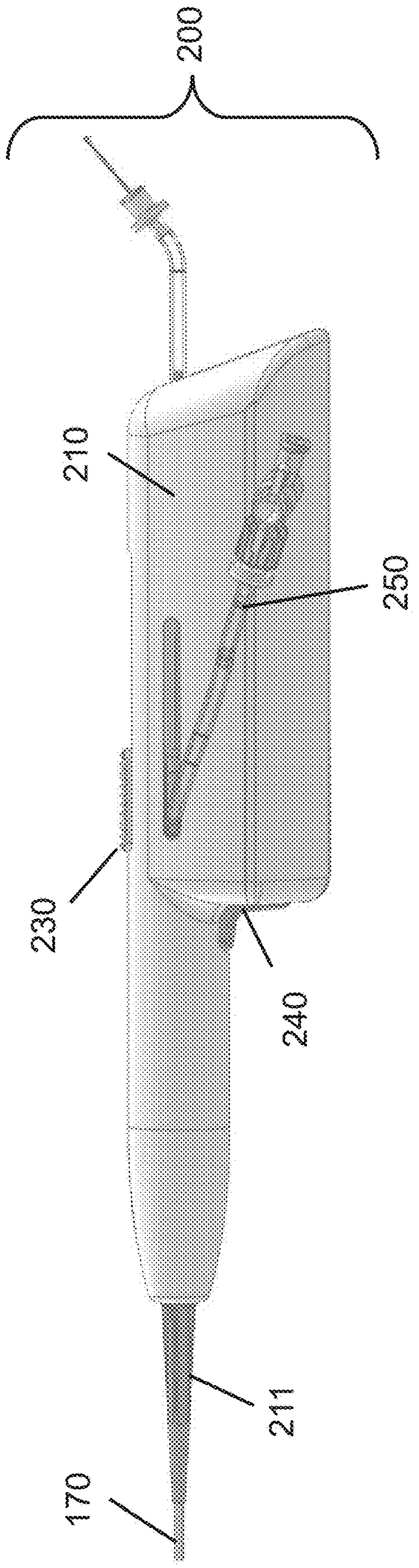
FIGS. 8A-8B are images of a handheld component of delivery device 200.
Figure 8B:
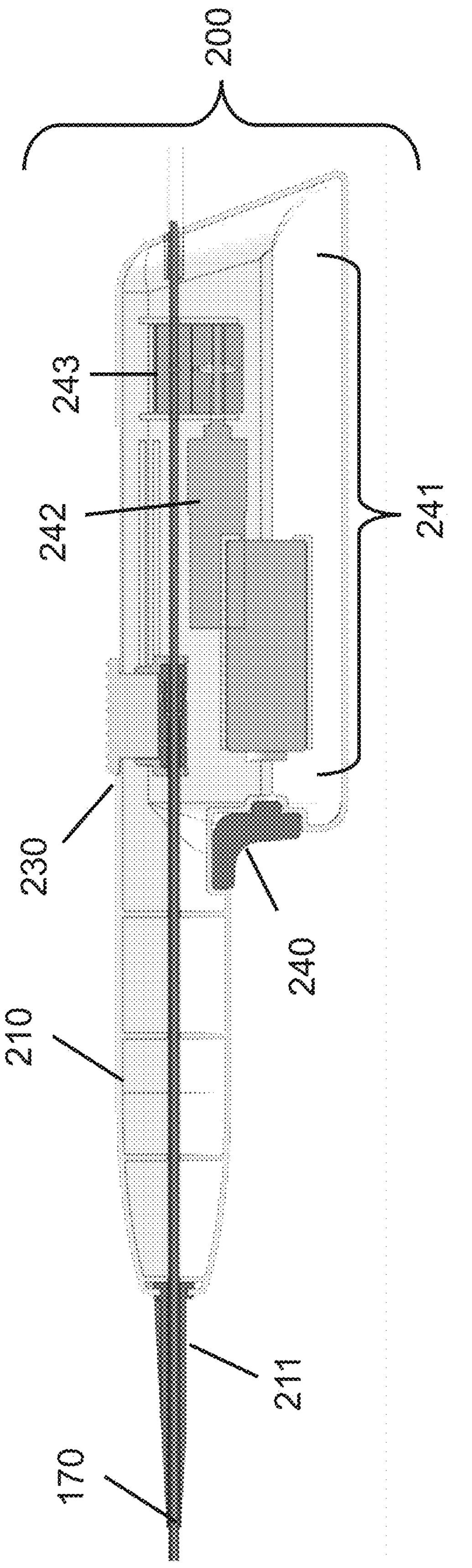
Figure 9A:
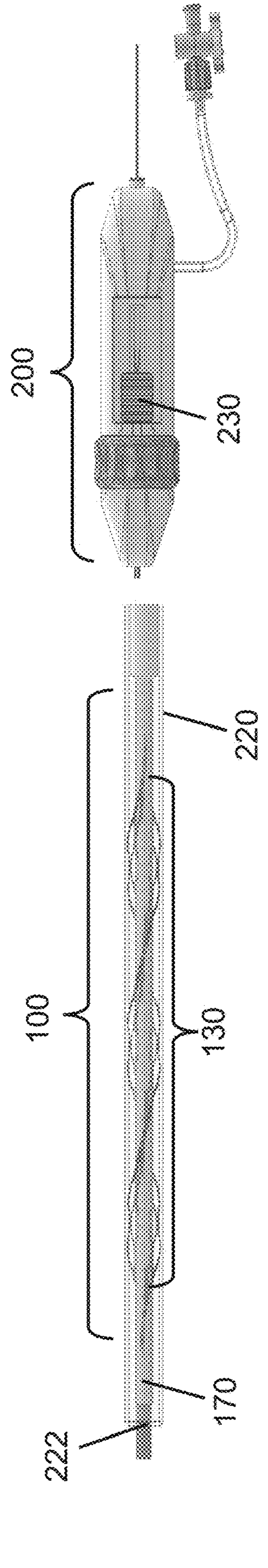
FIGS. 9A-9D are images showing the decompression and deployment of helical lattice 130 of thrombectomy device 100 within sheath 220 as deployment mechanism 230 is operated.
Figure 9B:
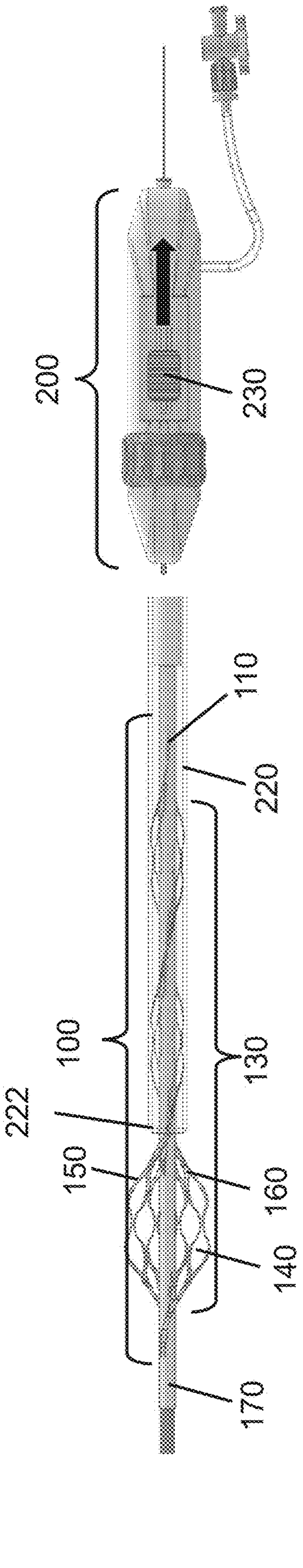
Figure 9C:
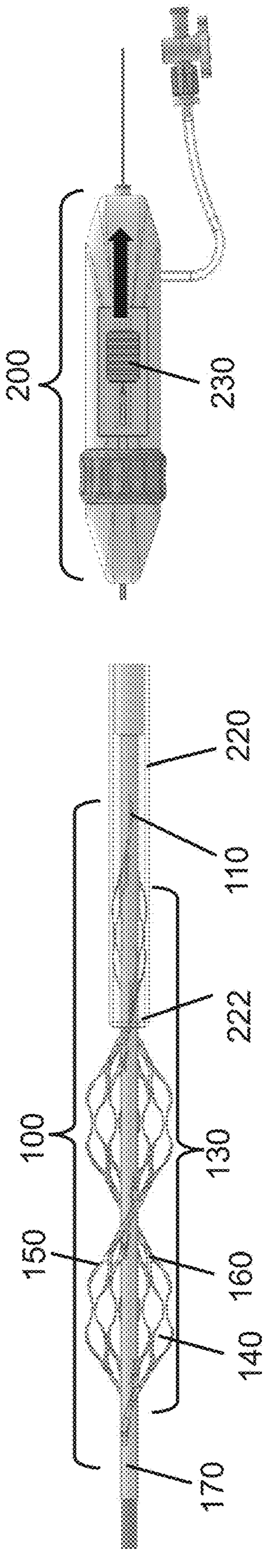
Figure 9D:
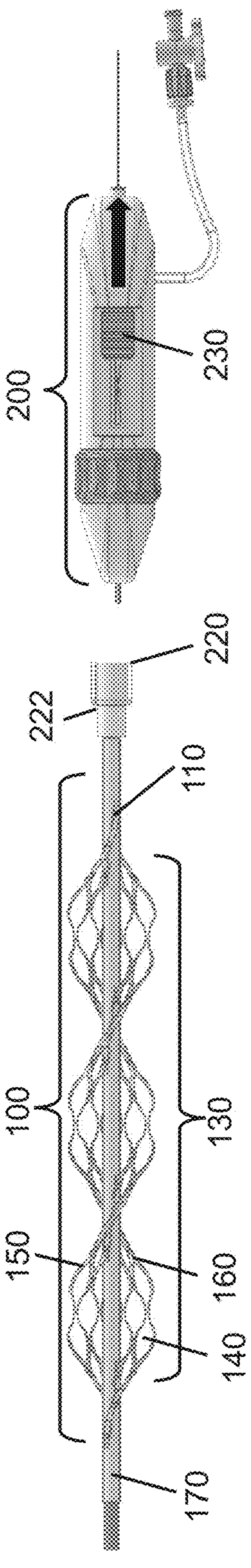

Housing 210 may include a hand-held portion that can be gripped by the operator of the thrombectomy device. Housing 210 may be fixedly attached to the proximal end of shaft 170, sheath 220 (e.g., proximal end 221 of sheath 220), deployment mechanism 230, and/or rotary actuator 240. Housing 210 may be configured to apply force (e.g., rotational force, a force to push delivery system 200 and thrombectomy device 100 through the vasculature, etc.). Housing 210 may include a hollow or partially hollow body, within which rotator 241 may be stored. When sheath 220 is retracted using deployment mechanism 230, a portion of sheath 220 may be stored in the hollow body of housing 210. Inlet port 250 may join with the lumen of sheath 220 within the body of housing 210. An example of housing 210 including sheath 220, deployment mechanism 230, rotary actuator 240, and inlet port 250 is shown in FIGS. 8A-8B.

Housing 210 may also include a means of reducing strain on any joining between housing 210 and shaft 170 or sheath 220 during bending. For example, housing 210 may include reinforced region 211. Reinforced region 211 may be a region of material encasing the region where shaft 170 or sheath 220 connect to housing 210. The material of reinforced region 211 may be slightly stiffer and/or less bendable than the material of either shaft 170 or sheath 220, thereby reducing the extent to which either shaft 170 or sheath 220 can bend relative to housing 210 during operation of thrombectomy device 100.

Sheath 220 consists of proximal end 221 and distal end 222, with a length therebetween and a lumen spanning the length of sheath 220. The lumen of sheath 220 may have a diameter of at most the width of the thrombectomy device (e.g., from about 1 mm to about 30 mm, from about 1 mm to about 20 mm, from about 5 mm to about 20 mm, from about 5 mm to about 15 mm. etc.) and an outer diameter less than the diameter of the vessel it is chosen to be operated in. Sheath 220 may be sized to store thrombectomy device 100 in the compressed state. Sheath 220 may have a length of at least the length of thrombectomy device (e.g., (e.g., at least 20 mm, at least 30 mm, at least 50 mm, at least 75 mm, at least 100 mm, at least 150 mm, at least 200 mm, at least 250 mm, at least 300 mm, at least 400 mm, at least 500 mm, at least 600 mm, etc.). Sheath 220 may span the length of shaft 170 (e.g., be of a length from about 1 cm to about 200 cm, from about 20 cm to about 175 cm, from about 30 cm to about 150 cm, from about 40 cm to about 125 cm, from about 50 cm to about 100 cm, about 75 cm, etc.).

Sheath 220 may be mechanically or electronically coupled to deployment mechanism 230. Operating deployment mechanism 230 (e.g., depressing, rotating, or sliding deployment mechanism 230) manipulates sheath 220, e.g., by retracting sheath 220 into the body of housing 220 or releasing sheath 220 from the body of housing 220 to cover or partial cover helical lattice 130 (e.g., after it has engaged with a thrombus). Operating deployment mechanism 230 may include sliding deployment mechanism along a groove in housing 210 parallel to shaft 170. Moving deployment mechanism 230 may cause a corresponding motion in sheath 220. For example, when deployment mechanism 230 is moved away from the proximal end of thrombectomy device 100 (e.g., towards the rear of housing 210), it may pull sheath 220 away from the proximal end of thrombectomy device 100, towards the rear of the housing, thereby releasing thrombectomy device 100. Exemplary operation of delivery system 200 including sheath 220 is as follows. Prior to deployment of thrombectomy device 100, sheath 220 envelopes thrombectomy device 100, including helical lattice 130 and sheath 170. Deployment mechanism 230 is then operated to retract sheath 220, thereby releasing helical lattice 130, thereby allowing thrombectomy device 100 to expand from the compressed state to the uncompressed state. FIGS. 9A-9D show the expansion of thrombectomy device 100 during varying stages of deployment of helical lattice 130. Delivery system 200 may include a plurality of components which may be suitable for manipulating sheath 220. For example, in addition to deployment mechanism 230, delivery device may include a further deployment mechanism configured for smaller (finer) increment control over the retracted sheath than what is otherwise provided by deployment mechanism 230.

Delivery system 200 may include rotary actuator 240 which is mechanically or electronically coupled to rotator 241 stored within the body of housing 240. Rotator 241 is configured to rotate shaft 170 and/or the guidewire, thereby rotating thrombectomy device 100 (e.g., rotation about the first axis). Rotator 241 may include a motor mechanically coupled to one or more gears in contact with shaft 170. Rotator 241 may rotate thrombectomy device 100 at a rate from about 0.5 rpm to about 5000 rpm. The rate of rotation may be constant, or it may be variable and adjusted by the operator, as needed, during a thrombectomy procedure. Any electrical components required to operate rotator 241 (e.g., circuitry required for electric coupling, a power source for rotator 241, etc.) may be included within the body of housing 210.

Thrombectomy device 100 can be integrated into a combined delivery system, optionally including a sheath and/or other components, as described herein, as has been done with other types of thrombectomy devices known in the art (see, e.g., U.S. Pat. Nos. 10,695,159; 10,786,268; 8,734,374; and 5,702,413 and U.S. patent application Ser. No. 12/704,492 the sheaths of which are incorporated by reference).

The delivery system may further include one or more of a pusher, a guidewire, and a catheter.

Aspirators and Infusers

The delivery system may include inlet port 250 in fluidic communication with the lumen of sheath 220. Inlet port 250 may be attached to housing 210 and may be in fluid communication with the lumen of sheath 220. Inlet port 250 may be used as an aspirator (e.g., to provide negative pressure to the vicinity of a thrombus) or as an infuser (e.g., to deliver a therapeutic agent to the vicinity of a thrombus). Inlet port 250 may be used as an aspirator in methods requiring aspiration of a thrombus (e.g., aspiration thrombectomy or suction thrombectomy). When Inlet port 250 is used as an infuser, the inlet port may be connected to a reservoir of a therapeutic agent.

Methods of performing aspiration or infusion during a thrombectomy procedure, as well as devices and components for achieving aspiration and infusion, are known in the art and can be readily applied to the construction and/or use of thrombectomy device 100 and delivery system 200 of the disclosure (see, e.g., U.S. Pat. Nos. 10,188,409 and 8,105,309; and U.S. patents application Ser. Nos. 15/233,870; and 15/266,233, the entire contents of which are incorporated by reference).

Methods of Use

Thrombectomy device 100 and delivery system 200, as described herein, can be used to treat an occluded vessel (e.g., a blood vessel containing a blood clot or thrombus), e.g., during a thrombectomy procedure. The method may be used to treat or prevent a disease, pathological condition, or disorder in the subject. Injuries, diseases, pathological conditions, or disorders which the present disclosure may be used in the treatment of include: thrombosis (including arterial thrombosis, venous thrombosis, and deep vein thrombosis, pulmonary embolisms, and arterial thrombosis), antiphospholipid antibody syndrome, prothrombin gene mutation, Factor V leiden mutation, protein deficiency (e.g., Protein C, Protein S, or ATIII, etc.), strokes, heart attacks, limb loss from amputation, paralysis, hormone imbalances (e.g., increased estrogen), compression from other organs and/or tumors on the vessel, sustained venous damage as a result of frequent venous access, or as a result of forming a fistula or graft. Additionally, the injury, disease, or disorder may be a result of prior medical treatment for an injury, disease, or disorder requiring treatment with, e.g., hormone therapy, antifibrinolytic drugs (e.g., aprotinin, tranexamic acid, etc.), chemotherapy drugs (e.g., cisplatin and tamoxifen), or endovascular procedures (e.g., angioplasty, atherectomy, stent removal, vein embolization, etc.). Thrombectomy device 100 may be used to break down or remove an occlusion (e.g., a blood clot or thrombus) in a substantially linear vessel. Thrombectomy device 100 may be used to break down or remove an occlusion (e.g., a blood clot or thrombus) in a substantially non-linear vessel (e.g., a tortious vessel).

The devices, systems, and methods described herein can be used to perform arterial thrombectomies. The devices, systems, and methods described herein can also be used to perform dialysis thrombectomies (e.g., a thrombectomy to remove a clot in a dialysis fistula).

The shape and configuration of thrombectomy device 100 allows for more efficient engagement with a thrombus. Helical lattice 130 and helical lattice cells 140 increase the number of contact points between thrombectomy device 100 and the thrombus, creating a higher cross section of the device, and improving adherence to the thrombus.

Thrombectomy device 100 may be fixedly attached to shaft 170, both of which can be enclosed within the lumen of sheath 220 (which can be engaged to cover thrombectomy device 100 and retracted to deploy thrombectomy device 100). When sheath 220 is engaged with thrombectomy device 100 (thereby forcing thrombectomy device 100 to adopt a compressed state), thrombectomy device 100 may then be guided through the vessel to the site of the thrombus. Thrombectomy device 100 may be passed through the thrombus or may be passed beyond the thrombus (e.g., thrombectomy device 100 and shaft 170 traverses the thrombus). Thrombectomy device 100 may then be deployed at either location by retracting sheath 220, e.g., by pulling back on sheath 220 (e.g., with deployment mechanism 230) while holding thrombectomy device 100 in place, by pushing forward on thrombectomy device while holding sheath 220 in place, or by pushing forward on thrombectomy device 100 while pulling back on sheath 220. Once removed from sheath 220, thrombectomy device 100 is able to convert from the compressed (deformed) state to the uncompressed state (non-deformed) state. Force may be applied (e.g., though a pusher or through housing 210) to shaft 170 to reposition thrombectomy device 100 as needed. This may be used to minimize contact between thrombectomy device 100 and the blood vessel walls and/or to optimize the relative orientations of thrombectomy device 100 and thrombus for thrombus removal.

Thrombectomy device 100 may be used to perform a mechanical thrombectomy. Once proximal to or in contact with the thrombus, thrombectomy device 100 may adhere to the thrombus. Helical lattice 130 may be modified to include a means of adhering to the thrombus, e.g., by having a coating 190 that includes an adhesive, barbs, fibers, etc. Alternatively, helical lattice may physically adhere to the thrombus by having one or more of lattice cells 140 engage with the thrombus. The dimensions of the uncompressed state may be designed to maximize the points of contact with the thrombus. Helical lattice 130 and helical lattice cells 140 increase the number of contact points between thrombectomy device 100 and the thrombus, creating a higher cross section of the device, and improving adherence to the thrombus. The dimensions of the thrombectomy device in the deployed state (e.g., the uncompressed state) may be designed to minimize the number of points of contact with the vessel walls. Once adhered to the thrombus, thrombectomy device 100 may be re-enveloped by sheath 220 (e.g., sheath 220 may be released from the body of housing 210, e.g., by deployment mechanism 230), which forces thrombectomy device 100 to adopt the compressed state. Thrombectomy device 100 may then be pulled out of the vasculature of the subject using shaft 170, thereby also removing the thrombus from the blood vessel. The process may be repeated one or more times until the thrombus is completely or substantially completely removed. The lattice may also be manually rotated one or more times during the thrombectomy procedure and prior to re-sheathing and removal of thrombectomy device 100 in order to improve engagement with the thrombus (e.g., the blood clot).

Alternatively, thrombectomy device 100 may be used to perform a rotational thrombectomy. In this use, thrombectomy device 100 may be guided distal to the thrombus, e.g., such that shaft 170 traverses the length of the thrombus. Thrombectomy device 100 may then be deployed, e.g., by retracting the sheath, and expanded from the compressed state to the uncompressed or the partially uncompressed state (depending upon the size of the vessel into which thrombectomy device 100 is deployed). Thrombectomy device 100 may then be activated to macerate the thrombus, e.g., by rotating thrombectomy device 100. Thrombectomy device 100 can be pulled back during rotation so that the thrombus (e.g., a clot) is macerated in a distal to proximal direction. The process breaks the thrombus into smaller material which may then be removed from the vessel or allowed to pass through the vasculature of the subject once released from the vascular site. Thrombectomy device 100 includes a mechanism (e.g., a rotator, which can be activated using an on/off switch located at the housing) for rotating helical lattice 130 about the first axis of thrombectomy device 100 (e.g., a motor). Thrombectomy device 100 may be held stationary along the long axis of the blood vessel while the device is moved non-parallel to the long axis of the blood vessel or may be moved parallel to the long axis of the blood vessel while helical lattice 130 is rotating. In such a method, the thrombectomy device may be moved without contacting the walls of the vessel (e.g., the size of the thrombectomy device may be selected for the particular vessel in which it will be used in order to avoid having the thrombectomy device scrape the side of the vessel during use).

Both mechanical and rotational thrombectomies may include the step of aspirating the thrombus using an aspirator. During aspiration, thrombectomy device 100 may be allowed to at least partially span the thrombus. The method may include repeated aspiration steps at a given suction intensity followed by a pause. The suction intensity of each aspiration step may be the same as one or more other suction intensities of a different aspiration step, or each aspiration step may use the same suction intensity. The suction intensities may be from about 1 kPa to about 150 kPa (e.g., from about 10 kPa to about 125 kPa, from about 20 kPa to about 100 kPa, from about 30 kPa to about 75 kPa, from about 40 kPa to about 50 kPa, etc.). Each aspiration step may be performed for a time between 1 second and five minutes. Aspiration may include at least two aspiration steps, e.g., at least three aspiration steps, at least four aspiration steps, at least five aspiration steps, at least six aspiration steps, at least seven aspiration steps, at least eight aspiration steps, at least nine aspiration steps, at least ten aspiration steps, etc.

The method may further include the step of delivering one or more therapeutic agents into the vicinity of the thrombus through an infuser. The one or more therapeutic agents may be administered before operation, during operation, or after operation.

An operator may use a guidewire or pusher to aid in the positioning of thrombectomy device 100. Alternatively, force may be applied to shaft 170 in order to reposition thrombectomy device 100 relative to the vasculature of the subject. An operator may choose to position thrombectomy device 100 to minimize contact of thrombectomy device 100 with the vessel wall (e.g., to contact the vessel wall at less than 5 locations, less than 4 locations, less than 3 locations, less than 2 locations, at one location, or does not contact the vessel wall).

Methods for operating thrombectomy devices are known in the art (see, e.g., U.S. Pat. Nos. 5,766,191, 10,251,739, 11,013,523, 11,026,708 and 10,117,671, and U.S. patent application Ser. No. 12/614,006, the entire contents of which are incorporated by reference), which methods can be readily applied to the operation of thrombectomy device 100 of this disclosure. In a preferred embodiment, the device does not damage blood vessels during operation.

Thrombectomy device 100 can be used to remove a thrombus in a blood vessel, such as those described in Table 1. The method may be modified by one skilled in the art, as known in the art, for use in one of the blood vessels described herein.

Thrombectomy device 100 can minimize the risk of damaging the endothelium, can prevent or reduce the formation of further thrombi, and can reduce spasming (e.g., by reducing the number of points of contact with the vessel wall, thereby reducing irritation and/or damage to the vessel wall). Lattice cells of the helical body of the thrombectomy device can be used to break up the thrombus into small(er) pieces (e.g., at most 50% the size of the original thrombus, at most 40% the size of the original thrombus, at most 30% the size of the original thrombus, at most 20% the size of the original thrombus, at most 10% the size of the original thrombus, at most 5% the size of the original thrombus, at most 1% the size of the original thrombus, etc.). Reduction in the size of a thrombus may reduce the risk of clinically significant embolization. In addition, the lattice cells can engage a portion of the thrombi within aneurysms and pull them into the main lumen of sheath 220 for effective maceration.

Kits

The disclosure also features kits including thrombectomy device 100 and one or more additional components, such as one or more catheters, guidewires, pushers, access sheathes, guiding sheathes, and/or cartridges for loading the thrombectomy device. The kit may also provide equipment for providing vascular access (e.g., a vascular access micro puncture set and access sheath; see, e.g., U.S. Pat. No. 11,027,104, the entirety of which is incorporated by reference). In some embodiments, the vascular access sheath is sheath 220.

Methods of Making

The disclosure also features methods of making a thrombectomy device. For example, a thrombectomy device described herein can be made by a variety of methods, including machining, additive manufacturing (3D-printing), laser cutting, shape setting, metal injection molding, or a combination thereof.

EXAMPLES

The following examples are put forth so as to provide those of ordinary skill in the art with a description of how the compositions and methods described herein may be used, made, and evaluated, and are intended to be purely exemplary of the invention and are not intended to limit the scope of the invention.

Example 1: Use of a Thrombectomy Device

Thrombectomy device 100 may be used to treat a clot in a subject in need thereof. Thrombectomy device can be maneuvered through the vasculature of a subject as described herein. Once in proximity of or in contact with the clot, thrombectomy device 100 may be deployed (e.g., disengaged from sheath 220) and allowed to convert from a compressed state to an uncompressed state. Thrombectomy device 100 can be used to mechanically entrap the clot (e.g., by pulling it back into sheath 220 by having lattice cells 140 of helical lattice 130 grip or adhere to the clot) or can macerate the clot into smaller pieces by rotating thrombectomy device 100 when in contact with the clot. Removal or maceration of the clot improves the condition of a subject by increasing blood flow through the vessel.

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments of the invention include those disclosed in International Patent Application No. PCT/US24/32280, incorporated herein by reference, which includes embodiments recited in the claims, as well as descriptions of the thrombectomy device and methods of use thereof.

Other embodiments are in the claims.

The invention claimed is:

1. A thrombectomy device comprising a proximal end and a distal end defining a first axis and having a length therebetween, wherein the thrombectomy device comprises:

a) a single centrally located shaft along the first axis, wherein the shaft has a proximal end and a distal end, wherein the shaft is configured for complete rotation about the first axis, and wherein the shaft comprises a plurality of segments, wherein each segment is from about 0.1 mm to about 10 mm in length, wherein adjacent segments of the plurality of segments are configured to rotate or bend independently of each other; and b) a helical lattice with a proximal end and a distal end along the first axis, wherein the proximal end of the helical lattice is attached to the distal end of the shaft and wherein the helical lattice:

i) comprises a width that extends along a second axis that is perpendicular to the first axis, ii) comprises a first outer edge and a second outer edge forming a double helix, wherein a network of hollow lattice cells is located between the first outer edge and the second outer edge, iii) comprises a texture located on an inner surface of the helical lattice, and iv) is configured to convert between a compressed state and an uncompressed state about the second axis, wherein, the first outer edge and the second outer edge of the helical lattice join at the proximal end of the helical lattice.

2. The thrombectomy device of claim 1, wherein the thrombectomy device is sized to traverse a blood vessel.

3. The thrombectomy device of claim 1, wherein the helical lattice comprises about 1 to about 25 turns, wherein each turn comprises a pitch from about 1 mm to about 50 mm.

4. The thrombectomy device of claim 1, wherein the lattice cells are compressible, and the helical lattice is self-expanding from the compressed state to the uncompressed state.

5. The thrombectomy device of claim 1, wherein the lattice cells comprise a polygonal, square, rectangular, triangular, diamond, circular, elliptical, oval, oblong, lens, asteroid, deltoid, slit, or amorphous shape.

6. The thrombectomy device of claim 1, wherein the helical lattice comprises a thickness from about 0.01 mm to about 1 mm.

7. The thrombectomy device of claim 1, wherein the width of the thrombectomy device is from about 1 mm to about 30 mm when the thrombectomy device is in the uncompressed state.

8. The thrombectomy device of claim 1, wherein the width of the thrombectomy device is periodic along the length.

9. The thrombectomy device of claim 1, wherein the length of the thrombectomy device is from about 10 mm to about 600 mm.

10. The thrombectomy device of claim 1, wherein the adjacent segments may be rotated or bent from about 0.01° to about 45° relative to each other.

11. The thrombectomy device of claim 1, wherein the length of the shaft is from about 1 cm to about 200 cm and the width of the shaft is from about 1 mm to about 30 mm.

12. The thrombectomy device of claim 1, wherein the helical lattice further comprises a radiopaque marker and/or a coating.

13. The thrombectomy device of claim 1, wherein the helical lattice comprises a shape memory material, wherein optionally the shape memory material is nitinol.

14. The thrombectomy device of claim 1, wherein the thrombectomy device and/or the shaft is enclosed within a sheath.

15. The thrombectomy device of claim 1, wherein the shaft interfaces with a housing comprising a sheath, a deployment mechanism configured to retract the sheath, a rotary configured to rotate the shaft and/or the thrombectomy device, and/or an inlet port.

16. A delivery system comprising:

(a) the thrombectomy device of claim 1; and (b) a housing comprising one or more of an inlet port, a pusher, a sheath, a deployment mechanism configured to retract the sheath into the body of the housing, and a rotator configured to rotate the thrombectomy device one or more times.

17. The delivery system of claim 16, wherein the sheath comprises a proximal end, a distal end, and a lumen, wherein the thrombectomy device and the shaft at the proximal end of the thrombectomy device is enclosed by the lumen.

18. The delivery system of claim 16, wherein the inlet port is configured to transmit negative pressure through the inlet port to a distal end of the sheath, and/or receive an infusion of a therapeutic agent therethrough and to transmit the therapeutic agent to a distal end of the sheath, wherein, optionally, the therapeutic agent is one or more of heparin, tPA, nitroglycerin, and calcium channel blockers.

19. The delivery system of claim 16, wherein the deployment mechanism is configured to retract the sheath, thereby releasing the thrombectomy device from the lumen of the sheath, and to redeploy the sheath, thereby returning the thrombectomy device into the lumen of the sheath.

20. The delivery system of claim 16, wherein the rotator comprises a motor and one or more gears.

21. A method of removing a thrombus from a blood vessel, comprising:

a) inserting the thrombectomy device of claim 1 in the compressed state into the blood vessel;

b) advancing the thrombectomy device through the blood vessel and into contact with the thrombus;

c) allowing the helical lattice of the thrombectomy device to convert to the uncompressed state; and d) retracting the thrombectomy device, thereby removing the thrombus, or rotating the thrombectomy device about the first axis one or more times, thereby disrupting the thrombus.

22. The method of claim 21, wherein the thrombectomy device is enclosed in the lumen of a sheath in step a), and after step b) and prior to step c), the sheath is retracted, thereby allowing the helical lattice of the thrombectomy device to convert to the uncompressed state.

23. The method of claim 21, further comprising aspirating the thrombus and/or administering a therapeutic agent to the thrombus.

24. A kit comprising the thrombectomy device of claim 1 and one or more of a catheter, a pusher, a sheath, and a housing, wherein the housing further comprises one or more of an inlet port, a sheath, a deployment mechanism configured to retract the sheath into the body of the housing, and a rotator configured to rotate the thrombectomy device.

* * * * *